United States Patent
Gerber et al.

(10) Patent No.: US 9,649,494 B2
(45) Date of Patent: May 16, 2017

(54) ELECTRICAL STIMULATION THERAPY BASED ON HEAD POSITION

(75) Inventors: Martin T. Gerber, Maple Grove, MN (US); Christopher Poletto, North Oaks, MN (US); Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1110 days.

(21) Appl. No.: 13/457,063

(22) Filed: Apr. 26, 2012

(65) Prior Publication Data

US 2012/0277833 A1    Nov. 1, 2012

Related U.S. Application Data

(60) Provisional application No. 61/481,032, filed on Apr. 29, 2011.

(51) Int. Cl.
*A61N 1/08* (2006.01)
*A61N 1/36* (2006.01)
*A61N 1/05* (2006.01)

(52) U.S. Cl.
CPC ....... *A61N 1/36139* (2013.01); *A61N 1/0526* (2013.01); *A61N 1/0551* (2013.01); *A61N 1/36128* (2013.01)

(58) Field of Classification Search
CPC ................ A61N 1/0526; A61N 1/0551; A61N 1/36128; A61N 1/36139
USPC ..................................... 607/62, 139
See application file for complete search history.

(56) References Cited

U.S. PATENT DOCUMENTS

| | | |
|---|---|---|
| 5,306,292 A | 4/1994 | Lindegren |
| 5,626,629 A | 5/1997 | Faltys et al. |
| 5,775,331 A | 7/1998 | Raymond et al. |
| 5,928,272 A | 7/1999 | Adkins et al. |
| 6,259,945 B1 | 7/2001 | Epstein et al. |
| 6,393,325 B1 | 5/2002 | Mann et al. |
| 6,473,644 B1 | 10/2002 | Terry, Jr. et al. |
| 6,587,724 B2 | 7/2003 | Mann |
| 6,622,048 B1 | 9/2003 | Mann et al. |
| 6,640,136 B1 | 10/2003 | Helland et al. |

(Continued)

FOREIGN PATENT DOCUMENTS

| | | |
|---|---|---|
| EP | 1181951 B1 | 3/2004 |
| WO | 2004064634 A1 | 8/2004 |

(Continued)

OTHER PUBLICATIONS

Office Action from U.S. Appl. No. 13/456,829, dated May 8, 2015, 12 pages.

(Continued)

*Primary Examiner* — Michael Carey
(74) *Attorney, Agent, or Firm* — Shumaker & Sieffert, P.A.

(57) ABSTRACT

Techniques and systems for determining a head position of a patient and controlling delivery of electrical stimulation to a target stimulation site based on the determined head position are described. In some examples, movement of the head of the patient may result in movement of a lead, through which the electrical stimulation may be delivered, relative to the target stimulation site. Thus, controlling delivery of the electrical stimulation based on the head position may improve the efficiency and efficacy of the electrical stimulation therapy.

38 Claims, 14 Drawing Sheets

(56) References Cited

U.S. PATENT DOCUMENTS

| | | | |
|---|---|---|---|
| 6,731,986 B2 | 5/2004 | Mann | |
| 7,065,412 B2 | 6/2006 | Swoyer et al. | |
| 7,104,965 B1 | 9/2006 | Jiang et al. | |
| 7,174,215 B2 | 2/2007 | Bradley | |
| 7,254,446 B1 | 8/2007 | Erickson et al. | |
| 7,317,944 B1 | 1/2008 | Overstreet | |
| 7,317,948 B1 | 1/2008 | King et al. | |
| 7,519,431 B2 | 4/2009 | Goetz et al. | |
| 7,567,840 B2 | 7/2009 | Armstrong | |
| 7,578,819 B2 | 8/2009 | Bleich et al. | |
| 7,643,881 B2 | 1/2010 | Armstrong | |
| 7,689,286 B2 | 3/2010 | Pastore et al. | |
| 7,711,419 B2 | 5/2010 | Armstrong et al. | |
| 2003/0073899 A1* | 4/2003 | Ruohonen | A61N 2/02 600/417 |
| 2003/0153959 A1 | 8/2003 | Thacker et al. | |
| 2004/0116978 A1 | 6/2004 | Bradley | |
| 2004/0158298 A1 | 8/2004 | Gliner et al. | |
| 2004/0167586 A1 | 8/2004 | Overstreet | |
| 2005/0107654 A1* | 5/2005 | Riehl | A61N 2/006 600/9 |
| 2005/0119714 A1 | 6/2005 | Sieracki et al. | |
| 2005/0222626 A1* | 10/2005 | DiLorenzo | A61N 1/3605 607/2 |
| 2005/0245987 A1 | 11/2005 | Woods et al. | |
| 2006/0074450 A1 | 4/2006 | Boveja et al. | |
| 2006/0085048 A1 | 4/2006 | Cory et al. | |
| 2006/0167498 A1 | 7/2006 | DiLorenzo | |
| 2006/0253174 A1 | 11/2006 | King | |
| 2007/0016097 A1 | 1/2007 | Farquhar et al. | |
| 2007/0043395 A1 | 2/2007 | Wei et al. | |
| 2007/0233194 A1 | 10/2007 | Craig | |
| 2007/0255320 A1 | 11/2007 | Inman et al. | |
| 2008/0086175 A1 | 4/2008 | Libbus et al. | |
| 2008/0147140 A1 | 6/2008 | Ternes et al. | |
| 2008/0234780 A1 | 9/2008 | Smith et al. | |
| 2008/0269812 A1 | 10/2008 | Gerber et al. | |
| 2008/0281381 A1 | 11/2008 | Gerber et al. | |
| 2009/0030493 A1 | 1/2009 | Colborn et al. | |
| 2009/0043352 A1 | 2/2009 | Brooke et al. | |
| 2009/0076561 A1 | 3/2009 | Libbus et al. | |
| 2009/0112281 A1 | 4/2009 | Miyazawa et al. | |
| 2009/0198294 A1 | 8/2009 | Rossing et al. | |
| 2009/0299214 A1 | 12/2009 | Wu et al. | |
| 2010/0010383 A1 | 1/2010 | Skelton et al. | |
| 2010/0010390 A1 | 1/2010 | Skelton et al. | |
| 2010/0010576 A1 | 1/2010 | Skelton et al. | |
| 2010/0010580 A1 | 1/2010 | Skelton et al. | |
| 2010/0010584 A1 | 1/2010 | Skelton et al. | |
| 2010/0010585 A1 | 1/2010 | Davis et al. | |
| 2010/0010586 A1 | 1/2010 | Skelton et al. | |
| 2010/0114204 A1 | 5/2010 | Burnes et al. | |
| 2010/0114221 A1 | 5/2010 | Krause et al. | |
| 2010/0121408 A1 | 5/2010 | Imran et al. | |
| 2010/0161007 A1 | 6/2010 | King | |
| 2010/0249875 A1 | 9/2010 | Kishawi et al. | |
| 2010/0262209 A1 | 10/2010 | King et al. | |
| 2012/0271382 A1* | 10/2012 | Arcot-Krishnamurthy | A61N 1/36053 607/62 |

FOREIGN PATENT DOCUMENTS

| | | |
|---|---|---|
| WO | 2006073393 A1 | 7/2006 |
| WO | 2009134478 A1 | 11/2009 |
| WO | 2009158389 A1 | 12/2009 |
| WO | 2010065146 A1 | 6/2010 |
| WO | 2010105261 A1 | 9/2010 |

OTHER PUBLICATIONS

Response to Office Action mailed Nov. 30, 2015, from U.S. Appl. No. 13/456,829, filed Feb. 29, 2016, 15 pages.

AFCP 2.0 Decision/Advisory Action/Examiner-Initiated Interview Summary from U.S. Appl. No. 13/456,829, dated Sep. 6, 2016, 10 pages.

Response to Office Action mailed May 18, 2016, from U.S. Appl. No. 13/456,829, filed Jul. 18, 2016, 12 pages.

Response to final Office Action mailed May 18, 2016, the Advisory Action mailed Aug. 5, 2016, and the AFCP 2.0 Decision/Advisory Action mailed Sep. 9, 2016, from U.S. Appl. No. 13/456,829, filed Sep. 15, 2016, 18 pages.

Office Action from U.S. Appl. No. 13/456,829, dated Nov. 30, 2015, 12 pages.

Final Office Action from U.S. Appl. No. 13/456,829, dated May 18, 2016, 15 pages.

Advisory Action from U.S. Appl. No. 13/456,829, dated Aug. 5, 2016, 4 pages.

Response to Office Action mailed May 18, 2016, from U.S. Appl. No. 13/456,829, filed Aug. 18, 2016, 18 pages.

U.S. Appl. No. 13/456,829, filed Apr. 26, 2012, entitled "Determining Nerve Location Relative to Electrodes,".

U.S. Appl. No. 13/456,969, filed Apr. 26, 2012, entitled "Dual Prophylactic and Abortive Electrical Stimulation,".

* cited by examiner

ELECTRICAL STIMULATION THERAPY BASED ON HEAD POSITION

This application claims the benefit of U.S. Provisional Application No. 61/481,032, entitled "ELECTRICAL STIMULATION THERAPY BASED ON HEAD POSITION," and filed on Apr. 29, 2011, the entire content of which is incorporated herein by reference.

TECHNICAL FIELD

The disclosure relates to implantable medical devices and, more particularly, to implantable medical devices for delivery of electrical stimulation therapy.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle disorders, or obesity. An electrical stimulation system typically includes one or more implantable medical leads coupled to an external or implantable electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient. The one or more electrodes located proximate to the target stimulation site may deliver electrical stimulation therapy to the target stimulation site in the form of electrical signals.

SUMMARY

In general, the disclosure is directed to automatically controlling delivery of electrical stimulation to a target stimulation site of a patient based on one or more parameters indicative of a head position of the patient. By automatically adjusting stimulation programs and/or stimulation parameters, a stimulator may provide stimulation that is responsive to changes in therapeutic efficacy that may occur when head position changes. In some examples, the positions of one or more components of a medical device implanted within the patient may change as a result of a change in the position of the patient's head. In examples in which the medical device includes electrodes positioned to deliver electrical stimulation to the target stimulation site, movement of the patient's head may result in a change in head position that causes movement of the electrodes from or toward the target stimulation site or movement of the target stimulation site from or toward the electrodes and, consequently, possible changes in efficacy of the electrical stimulation therapy. In some examples, controlling delivery of electrical stimulation based on a parameter indicative of the patient's modified head position may help maintain, reestablish or improve the efficacy of the electrical stimulation therapy.

In one example, the disclosure is directed to a system that includes a processor configured to determine a head position of a patient and control delivery of electrical stimulation to a target stimulation site based on the determined head position.

In another example, the disclosure is directed to a method that includes determining a head position of a patient and controlling delivery of electrical stimulation to a target stimulation site based on the determined head position.

In another example, the disclosure is directed to a system that includes means for determining a head position of a patient and means for controlling delivery of electrical stimulation to a target stimulation site based on the determined head position.

In another example, the disclosure is directed to a non-transitory computer-readable medium comprising instructions that cause a processor to determine a head position of a patient and control delivery of electrical stimulation to a target stimulation site based on the determined head position.

In another example, the disclosure relates to a non-transitory computer-readable storage medium comprising instructions. The instructions cause a programmable processor to perform any part of the techniques described herein. The instructions may be, for example, software instructions, such as those used to define a software or computer program.

The details of one or more examples are set forth in the accompanying drawings and the description below. Other features, objects, and advantages of the disclosure will be apparent from the description and drawings, and from the claims.

DETAILED DESCRIPTION

Figure 1A:
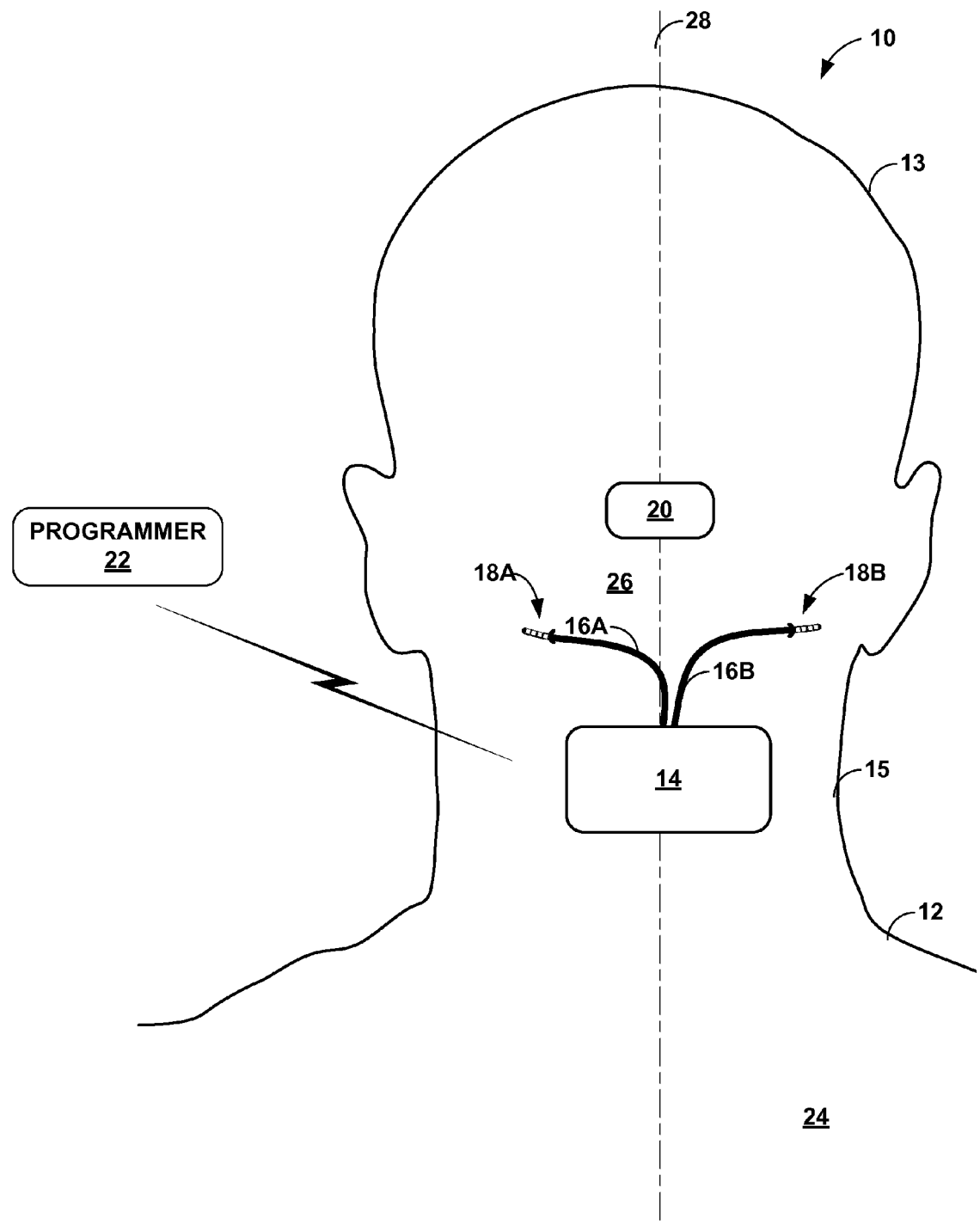
FIGS. 1A and 1B are conceptual diagrams illustrating example therapy systems for delivering electrical stimulation to alleviate an occipital nerve disorder of a patient.

Implantable medical devices (IMDs) that deliver electrical stimulation therapy may be implanted proximate to a target stimulation site, such as a particular nerve or muscle. For example, one or more electrodes of an IMD may be implanted proximate to a nerve that is known to influence or affect the disorder of the patient. In some examples, particular ones of a plurality of electrodes of the IMD may be implanted proximate to particular portions of the target nerve in order to most effectively and efficiently treat the disorder of the patient. The electrodes may be arranged to deliver stimulation via monopolar, bipolar, or multipolar electrode configurations.

Electrical stimulation of a peripheral nerve, such as stimulation of an occipital nerve, may be used to mask a patient's feeling of pain with a tingling sensation, referred to as paresthesia. Occipital nerves, such as a lesser occipital nerve, greater occipital nerve, or third occipital nerve, exit the spinal cord at the cervical region, extend upward and toward the sides of the head, and pass through muscle and fascia to the scalp. Pain caused by an occipital nerve, e.g. occipital neuralgia, may be alleviated by delivering electrical stimulation therapy to the occipital region via an implanted stimulation lead.

As an example, one or more electrodes of an IMD may be implanted proximate to an occipital nerve of the patient to treat occipital neuralgia that causes head, neck, and/or facial pain or tension for the patient. In some examples, the IMD may include one or more leads that are implanted transversely across the occipital nerve such that a portion of the lead is directly in contact with the occipital nerve. Each of the leads may include a plurality of electrodes, and delivery of stimulation via the plurality of electrodes may be evaluated with respect to the occipital nerve to determine which of the plurality of electrodes may be most effective and efficient in stimulating the nerve. Thus, some electrodes of the IMD may be positioned with respect to the occipital nerve to deliver stimulation to the occipital nerve with greater efficacy than other electrodes.

In some examples, movement of the patient's head, causing a change in head position, may result in movement of the lead relative to the target stimulation site (e.g., a target nerve), to varying degrees. Relative movement between the target stimulation site (e.g., particular tissue layers or particular nerves of the target stimulation site) and the lead may, in some examples, result in a change in the stimulation field produced by one or more stimulation electrodes of the lead, and/or the effect of the stimulation field on the target stimulation site, either of which may affect the efficacy and/or efficiency of the electrical stimulation therapy in treating the disorder of the patient. In some examples, adjusting the electrical stimulation therapy in response to such relative movement between the target stimulation site and the lead may help to maintain more consistent stimulation of the target stimulation site to more effectively treat the disorder of the patient.

The selection of programs or adjustment of parameters may result in application of different stimulation parameters for different sensed parameters that are indicative of head position, i.e., correlated with head position. The parameters may include, for example, different voltage or current amplitudes, pulse widths, pulse rates, electrode combinations and/or electrode polarities. Different electrode combinations and polarities, in some examples, may be selected to move a stimulation field in response to relative movement between a target stimulation site and the electrodes, which may occur with changes in head position. For example, stimulation delivered via a first combination of electrodes may be shifted by moving to a different combination of electrodes based on a change in relative positioning between the target stimulation site and the electrodes, consistent with a sensed parameter indicative of head position.

In examples in which particular electrodes of the IMD are selected to deliver stimulation to a particular portion of a nerve, e.g., an occipital nerve, movement of the lead resulting from movement of the patient's head may change the efficiency and/or efficacy of the stimulation delivered to the target nerve by changing the positioning of the particular electrodes relative to the nerve. For example, movement of the lead may shift a particular electrode away from the target nerve or toward the target nerve. In this case, it may be desirable to increase or decrease stimulation intensity if the same electrode or electrodes are used for delivery of stimulation. In particular, if one or more stimulation electrodes moves away from the target nerve, an increase in stimulation intensity may be desirable, but at the expense of increased power consumption. If one or more stimulation electrodes move toward the target nerve, a decrease in stimulation may be desirable. Alternatively, one or more different electrodes may become more desirable for delivery of stimulation. Hence, when head position changes, it may be desirable to select a different electrode configuration, e.g., to spatially shift the stimulation field in a particular direction, e.g., toward or away from the target stimulation site, depending on the direction of head position and the resulting change in relative positioning between the target stimulation site and the electrodes.

In these examples, in order to maintain, reestablish and/or improve the efficacy and efficiency of the electrical stimulation therapy, one or more components of the therapy system may determine a head position of the patient, or a parameter that correlates with or is otherwise indicative of head position, and subsequently control delivery of the electrical stimulation, e.g., by modifying one or more parameters defining the electrical stimulation, such as parameters that contribute to stimulation intensity, or by modifying the particular electrodes used to deliver the stimulation, or by modifying both parameters and particular electrodes. In each case, stimulation delivered to the target stimulation site is automatically controlled, e.g., by a programmer or stimulator, at least in part based on the determined head position of the patient. In particular, the programmer or stimulator may be configured to sense a parameter indicative of head position and automatically select a stimulation program and/or automatically adjust one or more stimulation parameters of a program based on the sensed parameter. In this manner, the stimulator, either independently or under control of a programmer, may be head-position responsive in the sense that it may be configured to automatically adjust stimulation in response to a parameter indicative of head positions, e.g., in an attempt to maintain stimulation efficacy over a variety of different head positions. Hence, different programs or parameters may be associated with different ranges of the parameter indicative of head position, and the associated programs or parameters may be automatically selected in response to the sensing of the corresponding parameters indicative of head position.

In the examples described herein, efficacy of the electrical stimulation therapy may refer to the effectiveness of the electrical stimulation therapy in alleviating symptoms of the patient's disorder, without causing undue side effects. For example, in examples in which electrical stimulation therapy is delivered to the occipital nerve(s) of the patient to treat occipital neuralgia, efficacious electrical stimulation therapy may result in alleviation of a large portion of the head, neck, and/or facial pain and/or tension of the patient without causing discomfort to the patient (e.g., uncomfortable tingling, pricking, or numbness of the head, neck, and/or face of the patient resulting from the electrical stimulation delivered to the occipital nerve(s) of the patient).

In the examples described herein, efficiency of the electrical stimulation therapy may refer to energy efficiency of the electrical stimulation therapy. For example, a first electrical stimulation therapy program may be more efficient than a second electrical stimulation therapy program if the first electrical stimulation therapy program requires less power than the second electrical stimulation therapy program to produce essentially the same level of efficacy in treating the disorder of the patient.

Although the examples described herein primarily refer to medical devices which may be fully implantable, in other examples, the medical devices may not be entirely implantable and may be partially or fully external. In addition, although the examples described herein primarily refer to electrical stimulation therapy, in other examples, the medical devices may deliver other types of therapy. For example, in some examples, the medical devices may include one or more fluid delivery components to deliver a fluid, e.g., a drug, to a target tissue site of a patient to treat a patient disorder.

FIG. 1A illustrates an example therapy system 10 configured to control delivery of electrical stimulation to patient 12 based on head position of patient 12. Patient 12 ordinarily will be a human patient. In some cases, however, therapy system 10 may be applied to other mammalian or non-mammalian, non-human patients. While occipital nerve disorders are primarily referred to herein, in other examples, therapy system 10 may alternatively or additionally provide therapy to manage symptoms of other patient conditions.

Therapy system 10 includes electrical stimulator 14 coupled to leads 16A and 16B (collectively "leads 16") implanted within patient 12. As illustrated, each of leads 16A and 16B includes a plurality of electrodes 18A and 18B, respectively, coupled to the distal end of the lead. As illustrated in FIG. 1A, therapy system 10 additionally includes sensing element 20 and external programmer 22.

As illustrated in FIG. 1A, system 10 includes external programmer 22. External programmer 22 wirelessly communicates with stimulator 14 to retrieve information related to data sensed by electrodes 18 or other components of therapy system 10. Additionally, external programmer 22 may wirelessly communicate with stimulator 14 to provide or retrieve information related to delivery of therapy to patient 12. Programmer 22 is an external computing device that a user, e.g., a clinician and/or patient 12, may use to communicate with stimulator 14. For example, programmer 22 may be a clinician programmer that a clinician uses to communicate with stimulator 14 in order to program one or more therapy programs for stimulator 14. Alternatively, programmer 22 may be a patient programmer that allows patient 12 to select programs and/or view and modify therapy parameters. In some examples, the clinician programmer may include more programming features than the patient programmer. In other words, in some examples, more complex or sensitive tasks may only be allowed by the clinician programmer to prevent an untrained patient from making undesired changes to stimulator 14.

Programmer 22 may be a handheld computing device with a display viewable by the user and an interface for providing input to programmer 22 (i.e., a user input mechanism). For example, programmer 22 may include a small display screen (e.g., a liquid crystal display (LCD) or a light emitting diode (LED) display) that presents information to the user. In addition, programmer 22 may include a touch screen display, keypad, buttons, a peripheral pointing device or another input mechanism that allows the user to navigate through the user interface of programmer 22 and provide input. If programmer 22 includes buttons and a keypad, the buttons may be dedicated to performing a certain function (e.g., a power button) or the buttons and the keypad may be soft keys that change in function depending upon the section of the user interface currently viewed by the user. Alternatively, the screen (not shown) of programmer 22 may be a touch screen that allows the user to provide input directly to the user interface shown on the display. The user may use a stylus or a finger to provide input to the display.

In other examples, programmer 22 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 22. A wireless adapter coupled to the computing device may enable secure communication between the computing device and stimulator 14.

When programmer 22 is configured for use by a clinician, programmer 22 may be used to transmit initial programming information to stimulator 14. This initial information may include hardware information, such as the type of leads 16, the arrangement of electrodes 18 on leads 16, the position of leads 16 within patient 12, the configuration of electrode arrays 18, initial programs defining therapy parameter values, and any other information the clinician desires to program into stimulator 14. Programmer 22 may also be capable of completing functional tests (e.g., measuring the impedance between any of electrodes 18 of leads 16).

In the example illustrated in FIG. 1A, stimulator 14 is implanted within neck 15 of patient 12, and leads 16 are coupled to stimulator 14. Electrodes 18A and 18B are positioned proximate to occipital nerves within occipital region 26 of head 13 and neck 15 of patient 12. In some examples, leads 16 are positioned such that electrodes 18A and 18B lay transversely across the occipital nerves of patient 12. In this way, one or more particular electrodes of the plurality of electrodes 18A and 18B may be positioned to deliver electrical stimulation therapy to the occipital nerves.

Occipital region 26 generally encompasses occipital nerve sites and trigeminal nerve sites of patient 12. The occipital nerve sites and trigeminal nerve sites may be, for example, an occipital nerve (e.g., a greater occipital nerve, lesser occipital nerve, third occipital nerve), a trigeminal nerve, tissue adjacent to the trigeminal or occipital nerves, or a nerve branching from the occipital and/or trigeminal nerves. Thus, reference to an "occipital nerve" or a "trigeminal nerve" throughout the disclosure also may include branches of the occipital and trigeminal nerves, respectively. In some examples, stimulation delivered within the occipital region 26 (i.e., in regions of patient 12 proximate to occipital nerves, trigeminal nerves, or other cranial nerves) may help alleviate pain associated with, for example, chronic migraines, cervicogenic headaches, occipital neuralgia or trigeminal neuralgia.

In other examples, one or more of electrodes 18 may be implanted proximate to and configured to deliver electrical stimulation therapy to a different nerve to treat the disorder of patient 12. For example, in some examples, one or more of electrodes 18 may be implanted proximate to and configured to deliver electrical stimulation therapy to a portion or branch of the frontal nerve of patient 12, such as a supraorbital nerve of patient 12.

In some examples, electrical stimulation therapy configured to treat occipital nerve disorders of patient 12, e.g., occipital neuralgia or chronic migraines, may be defined by particular parameters that have been predetermined to be effective in treating the occipital nerve disorder of the patient 12. As an example, electrical stimulation therapy configured to treat occipital nerve disorders of the patient 12 may be defined by the following exemplary parameters.

1. Pulse Rate: between approximately 4 Hz and approximately 1200 Hz, more preferably between approximately 4 Hz and approximately 130 Hz, and still more preferably between approximately 40 Hz and approximately 60 Hz.
2. Amplitude: between approximately 0.1 volts and approximately 10.5 volts. In other examples, a current amplitude may be defined as the charge flow into a biological load driven by a delivered voltage. For example, the range of current amplitude may be between approximately 0.1 milliamps (mA) and approximately 20 mA.
3. Pulse Width: between approximately 10 microseconds and approximately 1000 microseconds, more preferably between approximately 100 microseconds and approximately 200 microseconds.

Although FIG. 1A illustrates stimulator 14 implanted within neck 15 of patient 12, in other examples, stimulator 14 may be implanted in another region of patient 12. For example, as illustrated in and described below with respect to FIG. 1B, a stimulator may be implanted within torso 24 of patient 12, and leads coupled to the stimulator may be tunneled through tissue of patient 12 to occipital region 26.

Electrical stimulator 14 generates a stimulation signal (e.g., in the form of electrical pulses or substantially continuous waveforms). The stimulation signal may be defined by a variety of programmable parameters, such as electrode combination, electrode polarity, stimulation voltage or current amplitude, stimulation waveform, stimulation pulse width, stimulation pulse frequency, and the like, and is delivered to occipital region 26 via leads 16 and, more particularly, via electrodes 18 carried by leads 16. The stimulation may be delivered via any of a variety of monopolar, bipolar, or multipolar electrode combinations. A monopolar combination may make use of the electrodes 18 on leads 16 and an electrode carried on a housing of stimulator 14.

Electrical stimulator 14 may also be referred to as a pulse or signal generator, or a neurostimulator. In some examples, one or more of electrodes 18 may also be a sense electrode or leads 16 may carry one or more additional sense electrodes to permit electrical stimulator 14 to sense electrical signals or other sensors to sense other types of physiological parameters (e.g., pressure, force, activity, temperature, or the like) from occipital region 26, respectively. In some examples, such sensed parameters may be recorded for later analysis, e.g., evaluation of stimulation efficacy, or used in the control of stimulation therapy or therapy parameters.

The proximal ends of leads 16 may be electrically and mechanically coupled to separate connection ports of electrical stimulator 14. In some examples, the connection ports may be located in a separate connector block within a housing of electrical stimulator 14. The connector blocks may include terminals at different axial positions within the connector block that mate with contacts at different axial positions at proximal ends of leads 16. The connection between leads 16 and the connection ports also includes fluid seals to prevent undesirable electrical discharge. In some examples, leads 16 may be removed from the connection ports by a clinician if desired. For example, the removable connection may be a pressure, friction, or snap-fit, e.g., with a spring contacts. In other examples, leads 16 may be fixed to the connection ports such that pulling on leads 16 will not ordinarily release them from the connection ports. Examples of relatively fixed connections include solder connections or set screws. In some examples, conductors disposed in the lead body of each of leads 16 electrically connect electrodes 18 to electrical stimulator 14.

In the example shown in FIG. 1A, electrodes 18A and 18B are implanted proximate to two target stimulation sites within the head 13 or neck 15 of patient 12 (e.g., proximate to one or more occipital nerves) on opposite sides of midline 28 of patient 12. Midline 28 is a schematic representation of the line that divides patient 12 into approximately equal and symmetrical left and right halves. Delivering electrical stimulation to two target stimulation sites may facilitate delivery of therapy to two nerve branches that branch from the same nerve. Nerves may branch into left and right branches that extend to opposite sides of midline 28, and therapy may be delivered to two nerve branches on opposite sides of midline 28. Stimulation of two nerve branches on opposite sides of midline 28 may be referred to as bilateral stimulation. However, bilateral stimulation may also refer to stimulation of any two regions of patient 12 either sequentially or simultaneously. Additionally, in some examples, delivering therapy after a nerve branch point, e.g., closer to the nerve endings, may allow more targeted therapy delivery with fewer side effects. In some examples, therapy may also be delivered unilaterally to one or more target stimulation sites. For example, stimulation therapy may be delivered to first and second target stimulation sites simultaneously or alternately or in an overlapping manner.

Although therapy system 10 is primarily described herein as delivering therapy to a target stimulation site within occipital region 26 of patient 12, in other examples, system 10 may be used in other neurostimulation applications. Thus, in other examples, target stimulation sites of patient 12 may be proximate to any other suitable nerve of patient 12. For example, leads 16 may be implanted proximate to other nerves and/or structures of the head and neck of patient 12. As another example, system 10 may be implanted at other locations in a patient and used for sacral stimulation, pelvic floor stimulation, peripheral nerve field stimulation, spinal cord stimulation, deep brain stimulation, gastric stimulation, or subcutaneous stimulation other than occipital stimulation. In each case, in accordance with some examples of this disclosure, the stimulation may be controlled based at least in part on a detected position of the patient's head, which may lead to movement of leads 16A, 16B relative to one another, relative to stimulator 14, and/or relative to target nerve sites.

In some examples, stimulator 14 includes a memory, which may store instructions defining a plurality of therapy programs that each defines a set of therapy parameter values. In some examples, stimulator 14 may select a therapy program from the memory based on various parameters. Stimulator 14 may subsequently generate electrical stimulation according to the therapy parameter values defined by the selected therapy program to manage symptoms associated with the disorder of patient 12. In some examples, in the memory, particular therapy programs may be associated with particular values for parameters indicative of various head positions of patient 12, and a processor of system 10 may access the memory to select the particular therapy programs based on the head position of patient 12, e.g., as detected by the measured values for the parameters. As mentioned above, the parameters may include pulse voltage or current amplitude, pulse rate, pulse width, electrode combination and electrode polarity.

Each of electrodes 18A and 18B may comprise a plurality of electrodes. Stimulator 14 is configured to deliver electrical stimulation via any electrodes of system 10. For example, in some examples, stimulator 14 may deliver bipolar electrical stimulation via two of electrodes 18A or 18B. In other examples, stimulator 14 may deliver unipolar electrical stimulation via any one of electrodes 18A or 18B and a housing electrode of stimulator 14. In yet other examples, stimulator 14 may deliver multipolar electrical stimulation via more than two of electrodes 18A and 18B. Other electrode configurations in which stimulator 14 delivers electrical stimulation via at least two electrodes of system 10 are contemplated.

During a trial stage in which stimulator 14 is evaluated to determine whether stimulator 14 provides efficacious therapy to patient 12, a plurality of therapy programs may be tested and evaluated for efficacy. Therapy programs may be selected for storage within stimulator 14 based on the results of the trial stage. During chronic therapy in which stimulator 14 is implanted within patient 12 for delivery of therapy on a non-temporary basis, stimulator 14 may generate and deliver stimulation signals to patient 12 according to different therapy programs. In addition, in some examples, patient 12 may modify the values of one or more therapy parameter values within a single given program or switch between programs in order to alter the efficacy of the therapy as perceived by patient 12 with the aid of programmer 22. Stimulator 14 or another component of system 10, e.g., programmer 22, may store instructions defining the extent to which patient 12 may adjust therapy parameters, switch between programs, or undertake other therapy adjustments. Patient 12 may generate additional programs for use by stimulator 14 via external programmer 22 at any time during therapy or as designated by the clinician.

Figure 11:
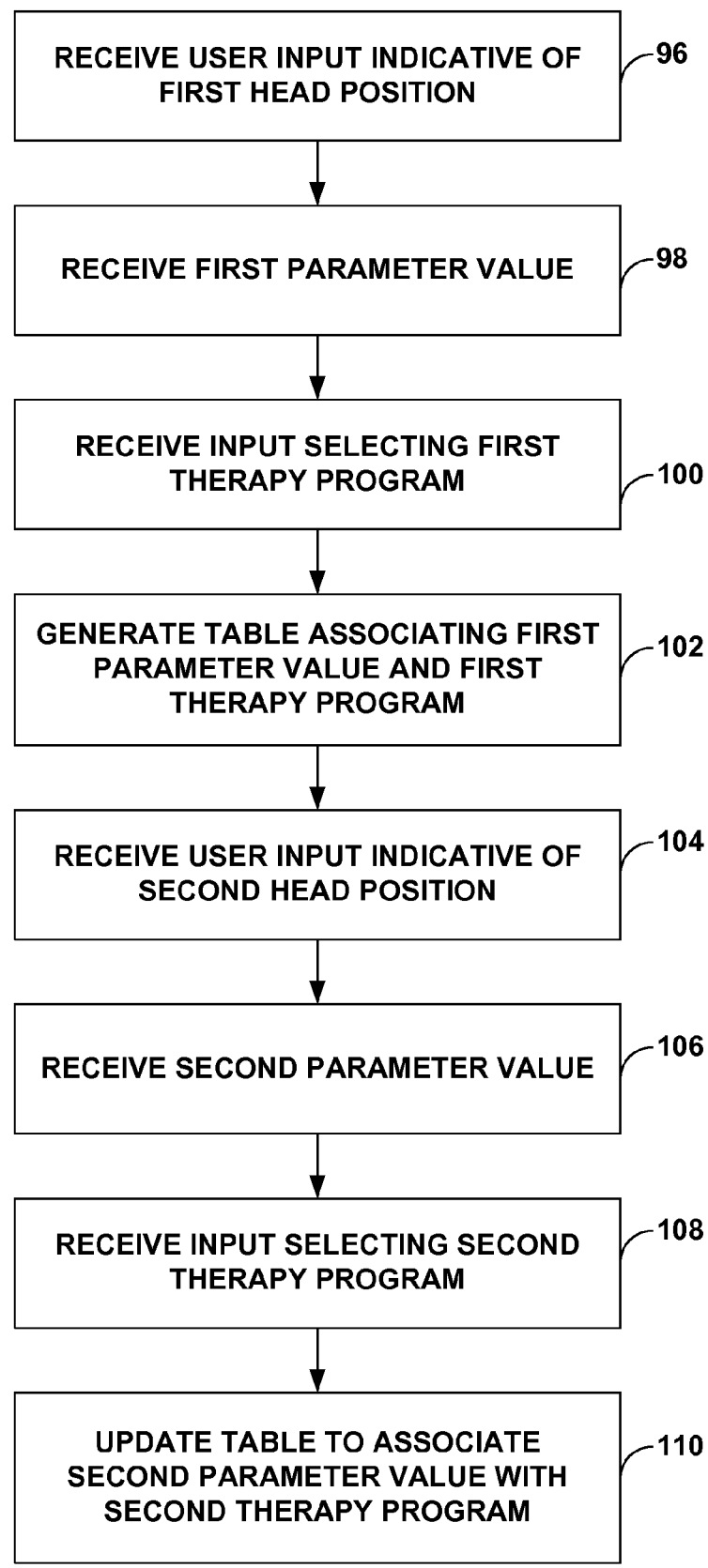
FIG. 11 is a flow diagram illustrating an example technique for generating a table that associates particular parameter values indicative of head position with particular therapy programs.

In some examples, as discussed with respect to FIG. 11, during the trial stage, a table or other data structure may be created, e.g., by stimulator 14 or programmer 22, associating various head positions of patient 12 with various therapy programs or parameter settings for such programs. For example, different programs, or combinations of programs delivered alternatively or simultaneously in time, may be selected for particular head positions based on perceived efficacy of such programs in alleviating symptoms when the patient occupies such head positions. Alternatively, or additionally, different parameter settings of a program or combination of programs may be selected based on perceived efficacy of such parameter settings for different head positions. The program and/or parameter settings may be selected by a clinician or patient during the trial stage and mapped to particular head positions in a table or other data structure, e.g., in stimulator 14 or programmer 22. The selections may be entered using programmer 22, which may be a patient programmer or a clinician programmer. Subsequently, during operation of stimulator 14, stimulator 14 or programmer 22 may select one or more therapy programs or parameter settings for delivery to patient 12 in response to one or more sensed head positions by accessing the table. The head position may be detected by stimulator 14 based on one or more sensed parameters indicative of head position.

As illustrated in FIG. 1A, therapy system 10 also includes sensing element 20. Sensing element 20 facilitates determination of the head position of patient 12 by a processor of system 10, such as a processor in stimulator 14 or a processor in programmer 22. For example, as discussed in detail with respect to FIGS. 4-7, sensing element 20 may directly or indirectly sense or facilitate sensing of a parameter value indicative of head position of patient 12 and the processor may determine the head position of patient 12 based on the parameter. Upon determining the head position of patient 12, system 10 can control stimulator 14 to deliver therapy to occipital region 26 that is selected for the determined head position of patient 12. As discussed previously, head position of patient 12 may correlate to relative movement of one or more of leads 16 with respect to the target stimulation site (e.g., as a result of movement of the leads 16 relative to the target stimulation site or movement of the target stimulation site relative to the leads), which may affect the efficacy of stimulation delivered via the leads 16 to the target stimulation site. Consequently, determining the head position of patient 12 and controlling stimulation, e.g., adjusting one or more stimulation parameters or selecting different stimulation programs, based on the head position may help to maintain efficacy of the stimulation therapy.

Head position of patient 12 may be defined in any suitable manner. In some examples, the position of head 13 may be referred to with respect to midline 28 of patient 12. For example, a head position of patient 12 may include a position in which head 13 is tilted to the left or to the right of midline 28. Similarly, head positions of patient 12 may include positions in which head 13 is tilted to the front, e.g., in a direction defined into the page of FIG. 1A, or tilted to the back, e.g., in a direction defined out of the page of FIG. 1A. In some examples, the head position may also include a component specifying a degree to which the head 13 is tilted in a particular direction. For example, a particular head position may specify that head 13 is tilted to the right at approximately thirty degrees from midline 28. In addition, in some examples, head position may be defined in part by a degree of rotation of head 13 about a central axis, e.g., the cervical spine, of the head. In particular, the head position may be defined by a particular combination of tilt and/or rotation. Additionally or alternatively, in some examples, the head position or a change in head position may be defined by a particular velocity or acceleration that is indicative of the velocity or acceleration with which patient 12 moved head 13. A quick head movement, for example, may cause an abrupt or rapid change in stimulation and perceived effects of stimulation, resulting in a perceived shock or jolt. Accordingly, in some examples, stimulation may be controlled not only based on a parameter indicative of head position, but a parameter indicative of the velocity or acceleration of head movement, such that different stimulation programs or parameters may be applied for different rates of change of head movement, e.g., rapid changes versus slower changes. In various examples, it may not be necessary to explicitly determine tilt, rotation angle, velocity, acceleration, and the like. Instead, it may be sufficient to sense a parameter that is indicative of, i.e., correlates to, head position and then map particular therapy parameter adjustments or programs to different ranges of such sensed parameters.

In some examples, such as the examples described below with respect to FIGS. 4 and 5, sensing element 20 may facilitate measurement of a parameter that correlates to the position of one or more of leads 16 relative to a fixed frame of reference, which correlates to the head position of patient 12. For example, in some examples, sensing element 20 may be anchored to the skull of patient 12, and therapy system 10 may measure one or more parameters, e.g., impedance or inductance, that correlate to the distance between the lead 16 and the anchored sensing element 20, which may be a function of head position. In this way, system 10 can detect movement of the lead (resulting from movement of the head) based on the one or more sensed parameters and, subsequently, appropriately control delivery of the electrical stimulation, e.g., by adjusting one or more parameters defining the electrical stimulation or selecting different stimulation programs, to occipital region 26. Again, the parameters may include amplitude, pulse rate, pulse width and/or the particular electrodes selected to deliver the stimulation, e.g., to permit the stimulation intensity and/or the location of the stimulation (by selection of particular electrode combinations), to be adjusted. It may not be necessary to explicitly determine head position. Instead, sensing a parameter that is indicative of, i.e., correlates to, head position, such as signals that are a function of variations in impedance or inductance due to lead movement, may be sufficient for control of stimulation.

In other examples, such as the examples described below with respect to FIGS. 6 and 7, sensing element 20 may facilitate measurement of a parameter that correlates to the actual position or motion of a portion of the body of patient 12. For example, sensing element 20 may be a motion and/or position sensor that measures the actual motion and/or position of head 13 of patient 12. In this manner, sensing element 20 may sense a parameter that is more directly indicative of head position. In some examples, particular motion/position measurement may be correlated with particular therapy parameters, and system 10 can control delivery of electrical stimulation by stimulator 14, e.g., by selecting particular therapy programs and/or adjusting stimulation parameters, based on the motion and/or position measurements sensed by sensing element 20. The selection of programs or adjustment of parameters may result in application of different parameters for different head positions. The parameters may include, for example, different voltage or current amplitudes, pulse widths, pulse rates, electrode combinations and/or electrode polarities. Different electrode combinations and polarities, in some examples, may be selected to shift stimulation spatially. For example, if stimulation is delivered via a first combination of electrodes for one head position, the stimulation may be shifted by moving to a different combination of electrodes, e.g., further away from or closer to a target stimulation site, given a particular change in head position, and hence a particular change in relative positioning between the target stimulation site and the electrodes. In some examples, the motion and/or position measurements may include measurements indicative of the absolute position of the head 13 of patient 12, measurements indicative of the position of head 13 relative to other portions of the body (e.g., torso 24) of patient 12, motion profiles of patient 12 indicative of a rate of change of one or more absolute or relative positions of head 13, and the like. In some examples, sensing element 20 may include one or more single and/or multi-axis accelerometer sensors configured to detect the movement and/or position of head 13 of patient 12.

The clinician may store therapy programs within stimulator 14 with the aid of programmer 22. During a programming session, the clinician may determine one or more therapy programs and associated parameter settings that provide efficacious therapy to patient 12. For example, the clinician may test and select one or more therapy programs that are efficacious in reducing or eliminating head, neck, and/or facial pain or tension resulting from occipital neuralgia of patient 12. During the programming session, patient 12 may provide feedback to the clinician as to the efficacy of the specific program and/or stimulation parameters being evaluated or the clinician may evaluate the efficacy based on one or more physiological parameters of patient 12 (e.g., heart rate, respiratory rate, or muscle activity). Programmer 22 may assist the clinician in the creation/identification of therapy programs by providing a methodical system for identifying potentially beneficial therapy parameter values.

Programmer 22 may also be configured for use by patient 12. When configured as a patient programmer, programmer 22 may have limited functionality (compared to a clinician programmer) in order to prevent patient 12 from altering critical functions of stimulator 14 or applications that may be detrimental to patient 12. In this manner, programmer 22 may only allow patient 12 to adjust values for certain therapy parameters or set an available range of values for a particular therapy parameter. In some examples, various operations in association with sensing head position and controlling delivery of therapy may be performed by a processor in stimulator 14, a processor in programmer 22, particularly when configured as a patient programmer, or both.

Programmer 22 may also provide an indication to patient 12 when therapy is being delivered, when patient input has triggered a change in therapy or when the power source within programmer 22 or stimulator 14 needs to be replaced or recharged. For example, programmer 22 may include an alert LED, may flash a message to patient 12 via a programmer display, generate an audible sound or somatosensory cue to confirm patient input was received, e.g., to indicate a patient state or to manually modify a therapy parameter.

Programmer 22 is configured to communicate with stimulator 14 and, optionally, another computing device, via wireless communication. For example, stimulator 14 may generate and wirelessly transmit signals to programmer 22 for display on the user interface of programmer 22. Programmer 22 may communicate via wireless communication with stimulator 14 using radio frequency (RF) telemetry techniques known in the art. Programmer 22 may also communicate with another programmer or computing device via a wired or wireless connection using any of a variety of local wireless communication techniques, such as RF communication according to the 802.11 or Bluetooth (R) specification sets, infrared (IR) communication according to the IRDA specification set, or other standard or proprietary telemetry protocols. Programmer 22 may also communicate with other programming or computing devices via exchange of removable media, such as magnetic or optical disks, memory cards or memory sticks. Further, programmer 22 may communicate with stimulator 14 and another programmer via remote telemetry techniques known in the art, communicating via a local area network (LAN), wide area network (WAN), public switched telephone network (PSTN), or cellular telephone network, for example.

In some examples, therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than stimulator 14. The external medical device may be coupled to percutaneous leads or to implanted leads via a percutaneous extension. If the trial stimulator indicates system 10 provides effective treatment to patient 12, the clinician may implant a chronic stimulator within patient 12 for relatively long-term treatment.

Figure 1B:
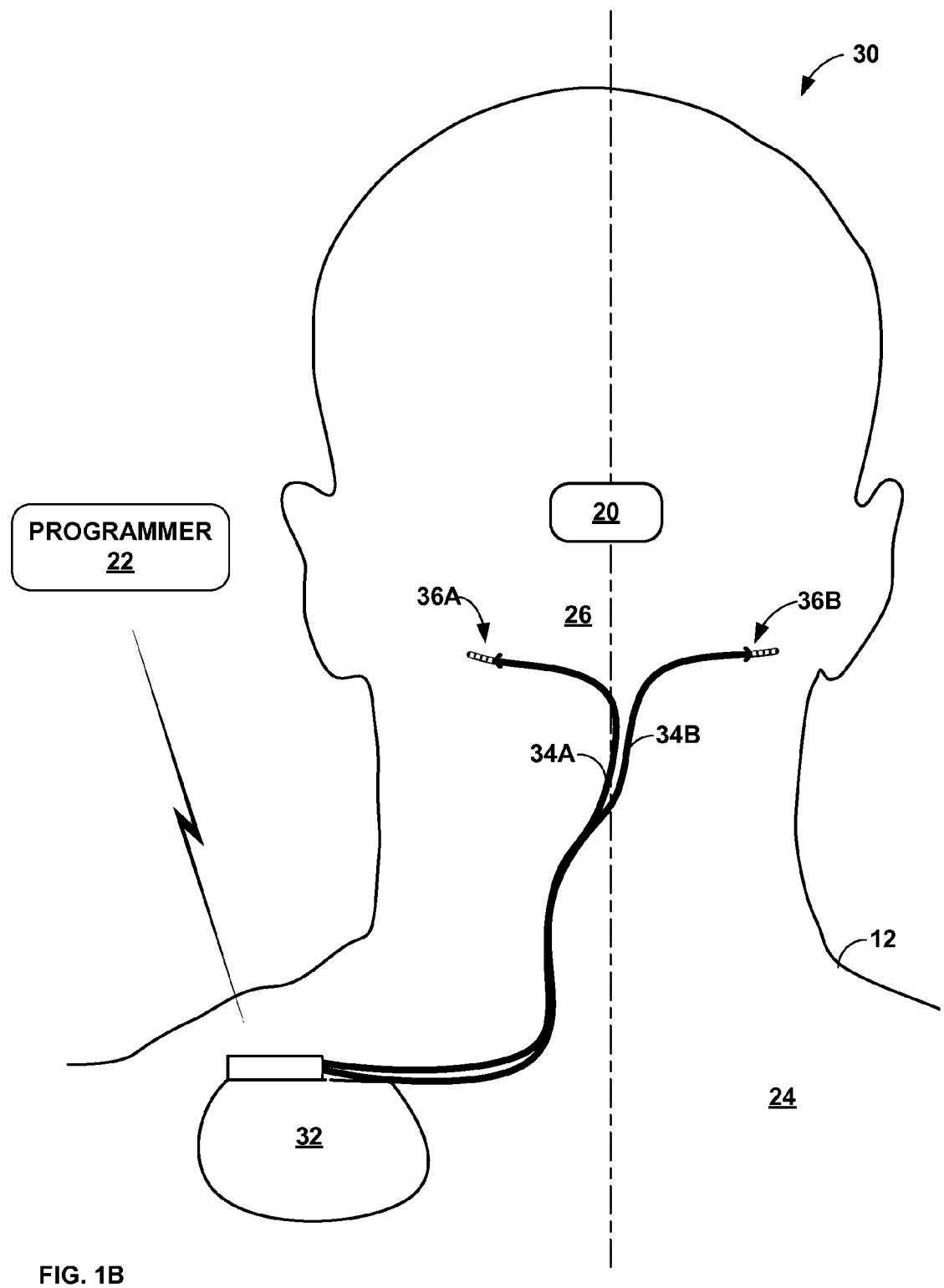

FIG. 1B illustrates an example therapy system 30 that includes stimulator 32, leads 34A and 34B (collectively "leads 34"), electrodes 36A and 36B (collectively "electrodes 36") coupled to the distal ends of leads 34A and 34B, respectively, sensing element 20, and programmer 22. Therapy system 30 is substantially similar to therapy system 10 illustrated in FIG. 1A. However, therapy system 30 includes stimulator 32 that is implanted within torso 24 of patient 12, and leads 34 that are tunneled through tissue of patient 12 such that one or more of electrodes 36A and 36B are positioned within occipital region 26 proximate to occipital nerves of patient 12. In other examples, the stimulator of therapy system 10 may be positioned within another portion of patient 12.

Figure 2:
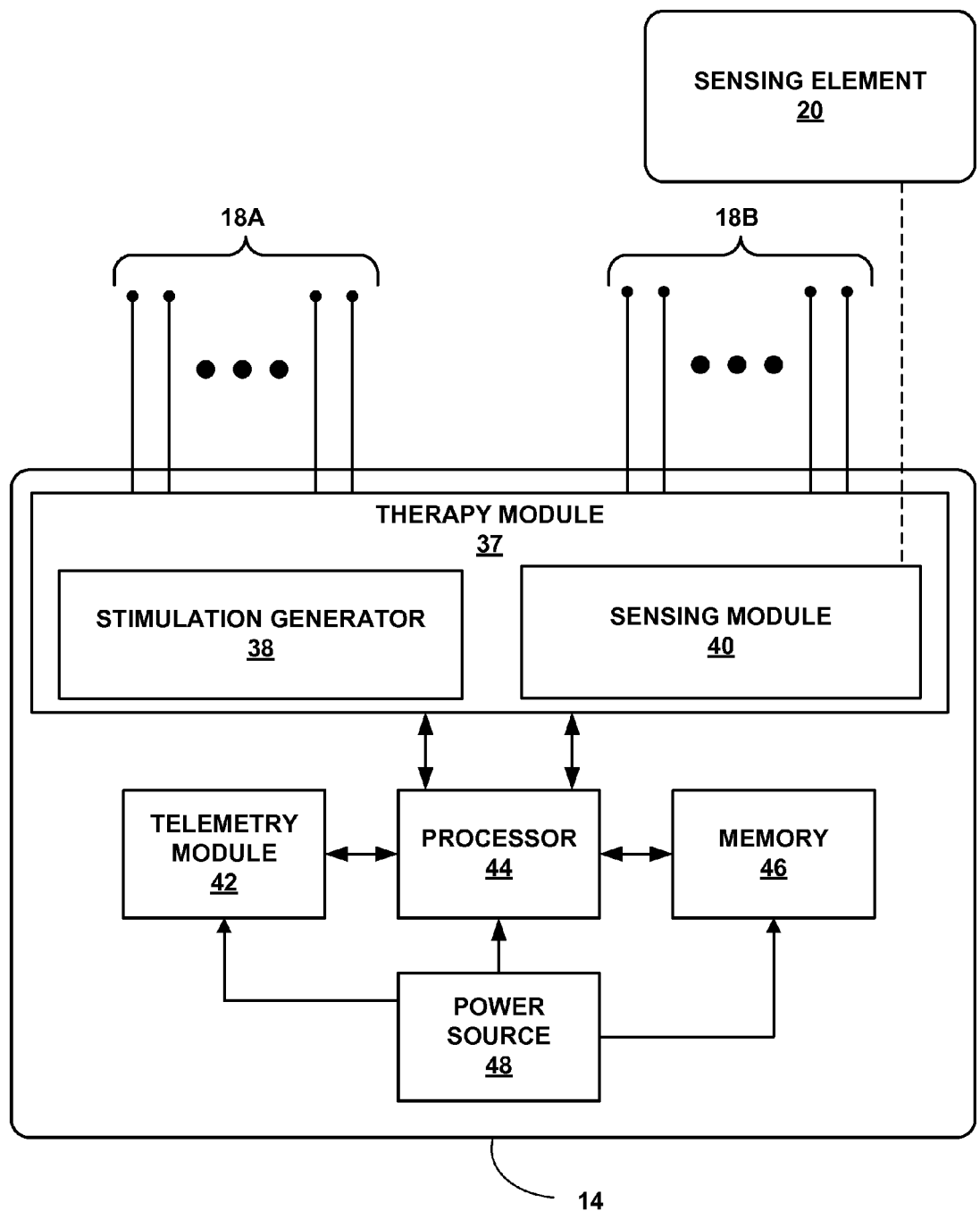
FIG. 2 is a functional block diagram illustrating example components of a therapy system.

FIG. 2 is a functional block diagram illustrating sensing element 20 and components of example stimulator 14. In the example illustrated in FIG. 2, stimulator 14 includes therapy module 37, which includes stimulation generator 38 and sensing module 40. As illustrated in FIG. 2, therapy module 37 is coupled to electrodes 18A and 18B. In this way, both stimulation generator 38 and sensing module 40 can transmit and receive signals via electrodes 18A and 18B. In addition, stimulator 14 includes telemetry module 42, processor 44, memory 46, and power source 48. As illustrated in FIG. 1A, stimulator 14 is coupled to electrodes 18A and 18B via leads 16A and 16B, respectively. FIG. 2 also illustrates sensing element 20, which, as illustrated, is configured to communicate with sensing module 40 of therapy module 37. Although FIG. 2 illustrates sensing element 20 as being separate from stimulator 14, in some examples, sensing element 20 may be integral with stimulator 14.

Processor 44 of stimulator 14 is configured to determine a head position of patient 12 and control delivery of electrical stimulation, e.g., via stimulation generator 38, to a target stimulation site of patient 12 based on the determined head position of patient 12. Processor 44 may include any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof Stimulation generator 38 is configured to generate and deliver electrical stimulation therapy to the target stimulation site of patient 12 (e.g., within occipital region 26) via one or more of electrodes 18A and 18B under the control of processor 44. Stimulation generator 38 may be a single channel or multi-channel stimulation generator. For example, stimulation generator 38 may be capable of delivering a single stimulation pulse, multiple stimulation pulses or a continuous signal at a given time via a single electrode combination or multiple stimulation pulses at a given time via multiple electrode combinations. In some examples, stimulation generator 38 may be configured to deliver electrical stimulation via multiple channels on a time-interleaved basis. For example, stimulator 14 may include a switch module configured to time divide the output of stimulation generator 38 across different combinations of eletrodes 18 at different times to deliver multiple programs or channels of stimulation energy to patient 12. In some examples, stimulator 14 may include separate voltage sources or separate current sources and sinks for each individual electrode (e.g., instead of a single stimulation generator) such that a switch module may not be necessary.

Sensing element 20 is configured to facilitate sensing of one or more parameters indicative of head position of patient 12 by sensing module 40, as described in further detail below with respect to FIGS. 4-7. In some examples, sensing element 20 may be positioned on or implanted within the head of patient 12 while, in other examples, sensing element 20 may be positioned on or implanted within another portion of the body of patient 12.

Sensing element 20 senses a signal that is either directly or indirectly indicative of head position. In some examples, sensing element 20 may sense a signal that directly correlates to the head position of patient 12 and transmit the signal to sensing module 40. For example, in some examples, sensing element 20 may be a motion and/or position sensor that generates an electrical signal that directly represents the motion and/or position of the head of patient 12. In other examples, sensing element 20 may generate an electrical signal that indirectly correlates to the head position of patient 12, and transmit the electrical signal to sensing module 40. For example, sensing element 20 may be an electrode that is anchored within the head of patient 12, and may contribute to generating an electrical signal between sensing element 20 and another electrode (e.g., one of electrodes 18), where the electrical signal is indicative of the proximity of sensing element 20 to the other electrode and corresponds to the head position of patient 12. In yet other examples, sensing element 20 may more passively facilitate sensing of head position of patient 12 by sensing module 40. For example, in some examples, sensing element 20 may be a stationary ferromagnetic object, anchored within patient 12, that modulates an electromagnetic field in accordance with the head position of patient 12, and the modulations of the field may correlate to the head position of patient 12. In other examples, sensing element 20 may be a reflective object that is configured to reflect light such that the reflectance varies in accordance with the amount of tissue and, consequently, the distance between lead 16 and the reflective sensing element 20. The object may include a material that is selectively reflective of light emitted from a lead tip. The light may be emitted by the lead tip, reflected by the object, and then sensed again at the lead tip as reflected light, where an amplitude or other characteristic indicates an amount of tissue, and hence movement, between the lead tip and object, thereby generally being correlated with head position or movement.

Sensing module 40 may be configured to receive and/or generate the information, e.g., electrical signal data, indicative of head position of patient 12 and transmit the information to processor 44. Processor 44 may be configured to analyze the information, and control delivery of electrical stimulation by stimulation generator 38 based on the information. For example, in some examples, sensing module 40 receives a value for a parameter defining an electrical signal that is representative of a particular head position of patient 12. Processor 44 may compare the sensed parameter value with one or more parameter values stored in memory 46, and subsequently select one or more stimulation therapy parameter values or therapy programs that correlate to the sensed parameter values. In some examples, processor 44 may compare the sensed parameter value to various ranges of parameter values stored in memory 46 to determine within which range the sensed parameter value falls, and may subsequently select particular stimulation therapy parameter values or therapy programs that correlate to the determined range of parameter values. Processor 44 may subsequently control stimulation generator 38 to deliver electrical stimulation to the target tissue site according to the selected stimulation therapy parameter values or therapy programs. In this way, processor 44 controls delivery of electrical stimulation based on a determined head position of patient 12. In some examples, processor 44 may continuously vary a stimulation parameter based on the head position of patient 12. For example, processor 44 may vary a stimulation parameter as patient 12 moves head 13 from one position to the next throughout the day. In particular, processor 44 may continuously vary a stimulation parameter from a value optimum for one position to a value optimum to a second position as the head moves from one position to the second. In some examples, processor 44 may control delivery of electrical stimulation by terminating or initiating delivery of the electrical stimulation. In each case, the programs or parameter adjustments may be selected based on a mapping of different ranges of the sensed parameter value to different programs or parameter adjustments. The mapping may be determined based on evaluation of efficacy of the programs or parameters for the patient over a range of different head positions.

In some examples, therapy system 10 may include sensors that sense additional parameters, in addition to parameters indicative of head position. For example, in some examples, therapy system 10 may include one or more sensors that indicate the overall posture of patient 12, e.g., whether patient 12 is lying down, standing up, sitting, etc. In these examples, processor 44 may control delivery of electrical stimulation to patient 12 based on the parameter indicative of head position and the parameter indicative of posture of patient 12. For example, processor 44 may determine that patient 12 has assumed a particular head position, based on the parameter indicative of head position, and a particular posture, based on the parameter indicative of posture. Also, sensing rotation of the patient's body may allow body to head relative motion to be determined, which may help avoid inappropriate stimulation changes when the patient's whole body is rotating instead of just the head. Processor 44 may subsequently select a therapy program or parameter adjustment that is associated with both the particular head position and the particular posture, and control stimulation generator 38 to deliver stimulation according to the selected therapy program. In some examples, therapy system 10 may include sensors that provide data related to other physiological parameters of patient 12, such as heart rate, and processor 44 may control delivery of electrical stimulation based on one or more of these parameters in combination with the parameter indicative of head position.

Although the examples herein are primarily described with respect to unilateral delivery of electrical stimulation to patient 12, the techniques are also applicable to bilateral delivery of electrical stimulation of patient 12. For example, processor 44 may determine a parameter indicative of head position of patient 12 on both sides of patient 12, e.g., via both of leads 16A and 16B, and individually control delivery of electrical stimulation via leads 16A and 16B. That is, in some examples, processor 44 may determine a first parameter indicative of head position of patient 12 via lead 16A and control delivery of electrical stimulation via lead 16A based on the first parameter indicative of head position of patient 12; similarly, processor 44 may determine a second parameter indicative of head position of patient 12 via lead 16B and control delivery of electrical stimulation via lead 16B based on the second parameter indicative of head position of patient 12. Bilateral sensing and stimulation may be particularly beneficial in examples in which the disorder of patient 12 relates to a type of nerve of which patient 12 has two or more distinct nerves, e.g., the occipital nerves or trigeminal nerves, as in the example illustrated in FIGS. 1A and 1B.

In some examples, the techniques described herein may also be applicable to shaping and/or steering of electrical stimulation fields generated by multiple electrodes of electrodes 18. For example, processor 44 may control a plurality, e.g., three, four, or more, of electrodes 18 to generate an electrical stimulation field extending outward from the plurality of electrodes 18 and defined by particular properties, e.g., a particular shape or direction, configured to deliver electrical stimulation to the target stimulation site to most effectively treat the disorder of patient 12. Based on the parameter indicative of head position of patient 12, and/or head position velocity or acceleration in some examples, processor 44 may control stimulation generator 38 to deliver electrical stimulation via the plurality of electrodes 18 (or via a different combination of electrodes 18) to shape and/or steer the electrical stimulation field in accordance with the determined parameter indicative of head position of patient 12. In some examples, processor 44 may control stimulation generator 38 to adjust parameters such as the electrode combination or an intensity defining the electrical stimulation to modify the size and/or shape of the electrical stimulation field generated by the electrodes.

Memory 46 may include any volatile or non-volatile media, such as a random access memory (RAM), read only memory (ROM), non-volatile RAM (NVRAM), electrically erasable programmable ROM (EEPROM), flash memory, and the like. Memory 46 may store computer-readable instructions that, when executed by processor 44, cause stimulator 14 to perform various functions described herein. In the example shown in FIG. 2, memory 46 may store look-up tables, predetermined therapy programs or therapy parameter sets, and other information in separate memories within memory 46 or separate areas within memory 46.

Telemetry module 42 supports wireless communication between stimulator 14 and an external programmer 22 or another computing device under the control of processor 42. Processor 42 of stimulator 14 may, for example, transmit signals indicative of head position of patient 12, therapy programs, and the like via telemetry module 42 to a telemetry module within programmer 22 or another external device. Telemetry module 42 in stimulator 14, as well as telemetry modules in other devices and systems described herein, such as programmer 14, may accomplish communication by radiofrequency (RF) communication techniques. In addition, telemetry module 42 may communicate with external programmer 14 via proximal inductive interaction of stimulator 14 with programmer 22. Accordingly, telemetry module 42 may send information to external programmer 22 on a continuous basis, at periodic intervals, or upon request from stimulator 14 or programmer 22.

Power source 48 delivers operating power to various components of stimulator 14. Power source 48 may include a small rechargeable or non-rechargeable battery and a power generation circuit to produce the operating power. Recharging may be accomplished through proximal inductive interaction between an external charger and an inductive charging coil within stimulator 14. In some examples, power requirements may be small enough to allow stimulator 14 to utilize patient motion and implement a kinetic energy-scavenging device to trickle charge a rechargeable battery. In other examples, traditional batteries may be used for a limited period of time.

Figure 3:
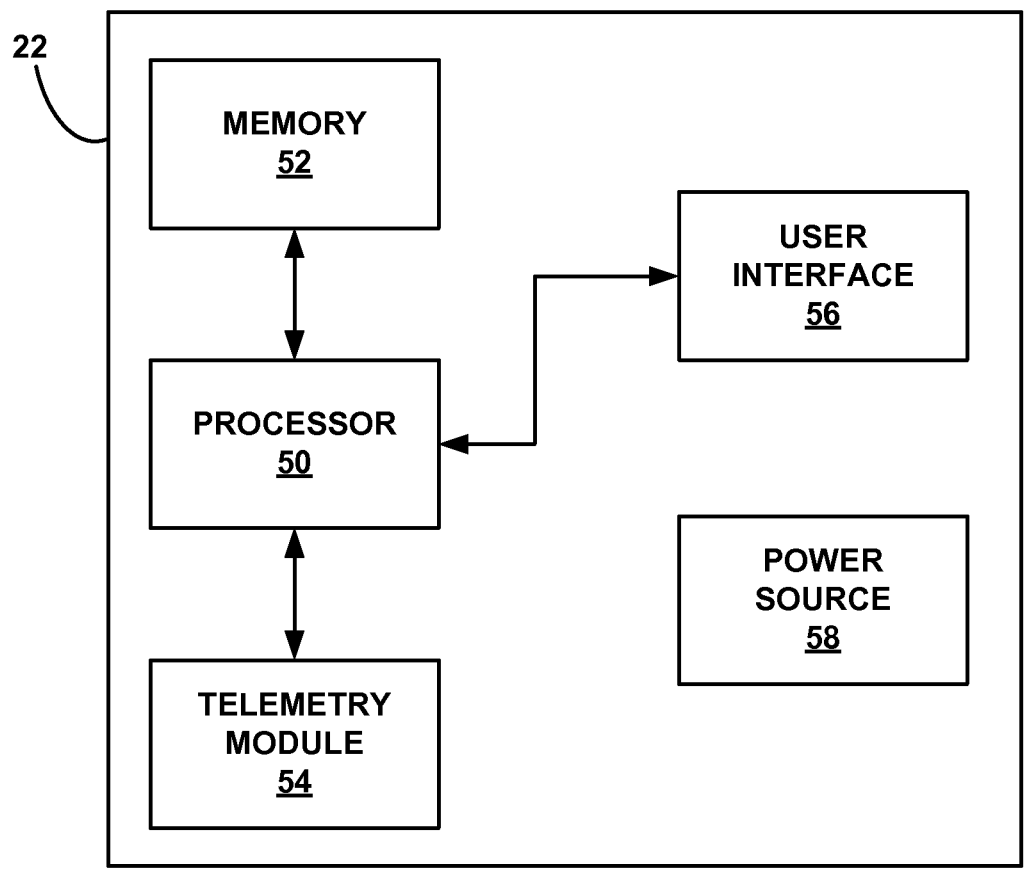
FIG. 3 is a functional block diagram illustrating example components of an external programmer.

FIG. 3 is a conceptual block diagram of an example external programmer 22, which includes processor 50, memory 52, telemetry module 54, user interface 56, and power source 58. Processor 50 controls user interface 56 and telemetry module 54, and stores and retrieves information and instructions to and from memory 52. Programmer 22 may be configured for use as a clinician programmer or a patient programmer. Processor 50 may comprise any combination of one or more processors including one or more microprocessors, DSPs, ASICs, FPGAs, or other equivalent integrated or discrete logic circuitry. Accordingly, processor 50 may include any suitable structure, whether in hardware, software, firmware, or any combination thereof, to perform the functions ascribed herein to processor 50.

A user, such as a clinician or patient 12, may interact with programmer 22 through user interface 56. User interface 56 includes a display (not shown), such as a LCD or LED display or other type of screen, to present information related to treatment of the medical disorder of patient 12. For example, user interface 56 may display electrical stimulation parameter values, therapy programs, tables, or the like via user interface 56. In some examples, the display may be used to present a visual alert to patient 12 that a head position of patient 12 has changed and that one or more electrical stimulation parameters will subsequently be modified. Other types of alerts are contemplated, such as audible alerts or somatosensory alerts. User interface 56 may also include an input mechanism to receive input from the user. In some examples, patient 12 may provide input via user interface 56 to approve or decline a suggested change in stimulation parameters. The input mechanisms may include, for example, buttons, a keypad (e.g., an alphanumeric keypad), a peripheral pointing device or another input mechanism that allows the user to navigate though user interfaces presented by processor 50 of programmer 22 and provide input.

If programmer 22 includes buttons and a keypad, the buttons may be dedicated to performing a certain function, i.e., a power button, or the buttons and the keypad may be soft keys that change function depending upon the section of the user interface currently viewed by the user. Alternatively, the screen (not shown) of programmer 22 may be a touch screen that allows the user to provide input directly to the user interface shown on the display. The user may use a stylus or their finger to provide input to the display. In other examples, user interface 56 also includes audio circuitry for providing audible instructions or notifications to patient 12 and/or receiving voice commands from patient 12, which may be useful if patient 12 has limited motor functions. Patient 12, a clinician or another user may also interact with programmer 22 to manually select therapy programs, generate new therapy programs, modify therapy programs through individual or global adjustments, and transmit the new programs to stimulator 14.

In some examples, at least some control of stimulation delivered to patient 12 may be implemented by processor 50. For example, processor 50 may receive information related to the head position of patient 12 and processor 50 may evaluate the information and control delivery of electrical stimulation, e.g., adjust one or more stimulation parameters, based on the information. Additionally or alternatively, a clinician may provide input to programmer 22, e.g., via user interface 56, to modify stimulation parameters based on the head position information, e.g., based on viewing the information via user interface 56.

In some examples, a user, e.g., patient 12 or a clinician, may utilize programmer 22 to generate the data that associates various parameters indicative of head position with various therapy programs and/or sets of therapy parameters. For example, in some examples, a user may record, e.g., via programmer 22, associations between the parameters indicative of head position and the therapy parameters/programs, e.g., as described below with respect to FIG. 11. In these examples, the user, e.g., a clinician, may instruct patient 12 to assume a variety a different head positions, initiate determination of the parameter indicative of head position for each of the variety of different head positions, and control delivery of electrical stimulation therapy to patient 12 for each of the variety of head positions until acceptable efficacy is achieved. The user may subsequently record, e.g., via programmer 22, each of the parameters indicative of head position with the corresponding electrical stimulation therapy parameters/programs. In other examples, the user may be patient 12, and patient 12 may enter therapy adjustments continuously, e.g., throughout his or her daily routine, via programmer 22. Presumably, patient 12 adjusts the electrical stimulation therapy until acceptable efficacy in treating the disorder of patient 12 is achieved. Upon receiving the therapy adjustments, processor 50 of programmer 22 may associate the resulting therapy program/parameter with the parameter indicative of head position of patient 12 at the time of therapy adjustment, and may utilize the association as a basis for controlling delivery of therapy or adjusting therapy parameters in the future. For example, when a parameter indicative of head position is sensed, stimulation programs or stimulation parameters previously associated with the parameter indicative of head position may be automatically selected by programmer 22 or stimulator 14 for delivery to patient 12.

As discussed herein, in some examples, a processor of system 10, e.g., processor 50, explicitly determines the head position of patient 12 based on the parameters indicative of head position of patient 12. In other examples, the processor may not explicitly determine the head position of patient 12 and may instead sense parameters that vary in accordance with variations in the head position of patient 12 and are, consequently, indicative of the head position of patient 12.

Memory 62 may include instructions for operating user interface 56 and telemetry module 54, and for managing power source 58. Memory 52 may also store any data retrieved from stimulator 14 during the course of therapy. Memory 52 may include any volatile or nonvolatile memory, such as RAM, ROM, EEPROM or flash memory. Memory 52 may also include a removable memory portion that may be used to provide memory updates or increases in memory capacities. A removable memory may also allow sensitive patient data to be removed before programmer 22 is used by a different patient.

Wireless telemetry in programmer 22 may be accomplished by RF communication or proximal inductive interaction of external programmer 22 with stimulator 14. This wireless communication is possible through the use of telemetry module 54. Accordingly, telemetry module 54 may be similar to the telemetry module contained within stimulator 14. In alternative examples, programmer 22 may be capable of infrared communication or direct communication through a wired connection. In this manner, other external devices may be capable of communicating with programmer 22 without needing to establish a secure wireless connection.

Power source 58 delivers operating power to the components of programmer 22. Power source 58 may include a battery and a power generation circuit to produce the operating power. In some examples, the battery may be rechargeable to allow extended operation. Recharging may be accomplished by electrically coupling power source 58 to a cradle or plug that is connected to an alternating current (AC) outlet. In addition, recharging may be accomplished through proximal inductive interaction between an external charger and an inductive charging coil within programmer 22. In other examples, traditional batteries (e.g., nickel cadmium or lithium ion batteries) may be used. In addition, programmer 22 may be directly coupled to an alternating current outlet to obtain operating power. Power source 58 may include circuitry to monitor power remaining within a battery. In this manner, user interface 56 may provide a current battery level indicator or low battery level indicator when the battery needs to be replaced or recharged. In some cases, power source 58 may be capable of estimating the remaining time of operation using the current battery.

In some examples, a processor of system 10, e.g., processor 44 or processor 50, may determine a parameter indicative of head position of patient 12, e.g., which directionally indicates head position or is a function of head position, based on a parameter indicative of the proximity of sensing element 20 to stimulator 14, lead(s) 16, and/or another component of system 10. The proximity of an anchored sensing element 20 to, for example, lead(s) 16 may be indicative of the head position of patient 12 because lead(s) 16 may move farther from or closer to the anchored sensing element 20 if patient 12 moves head 13 from position to position. Thus, in some examples, sensing element 20 may be anchored within patient 12 such that sensing element 20 creates a stable reference point, and the distance between anchored sensing element 20 and another component of system 10 may be measured based on a particular parameter and correlated to the head position of patient 12. For example, sensing element 20 may be anchored to the skull of patient 12, which may provide a stable reference point from which the proximity to lead 16 may be determined and subsequently correlated to the head position of patient 12. As discussed herein, in some examples, a processor of system 10 may not explicitly determine the head position of patient 12. Instead, the processor may determine a parameter that varies with variations in head position of patient 12, and/or a parameter that varies according to velocity of acceleration of movement of the head.

Figure 4A:
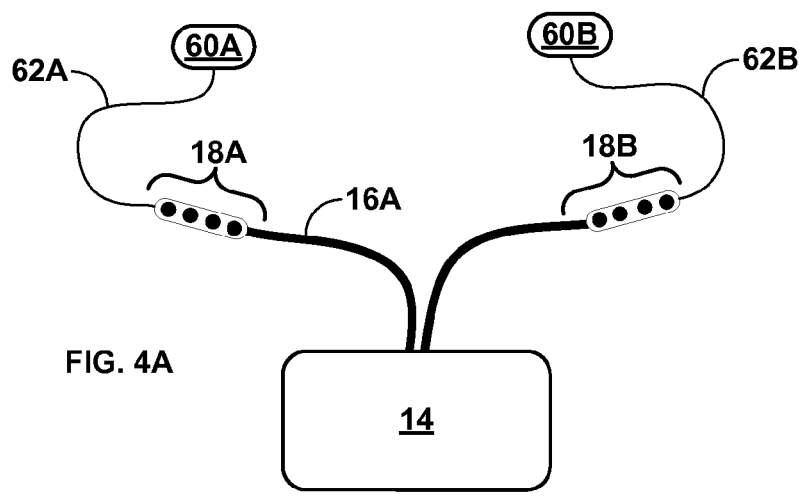
FIGS. 4A-4C are conceptual diagrams illustrating example configurations for therapy systems that include one or more sensing elements configured to facilitate sensing of a parameter indicative of head position of the patient.
Figure 4B:
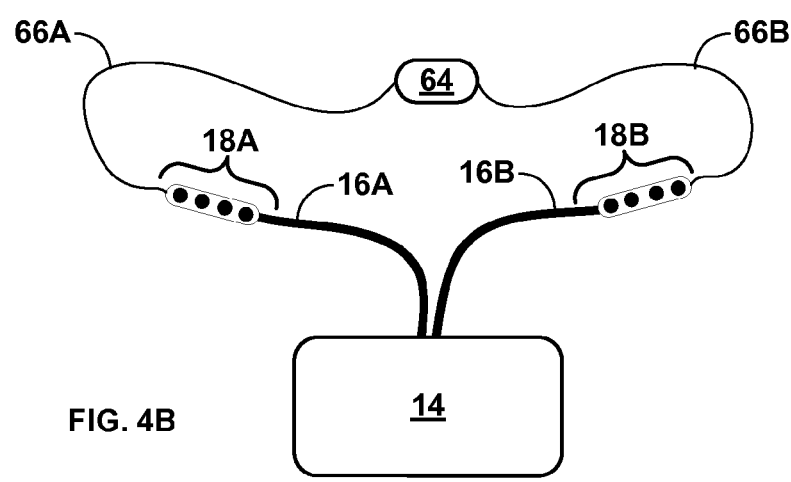
Figure 4C:
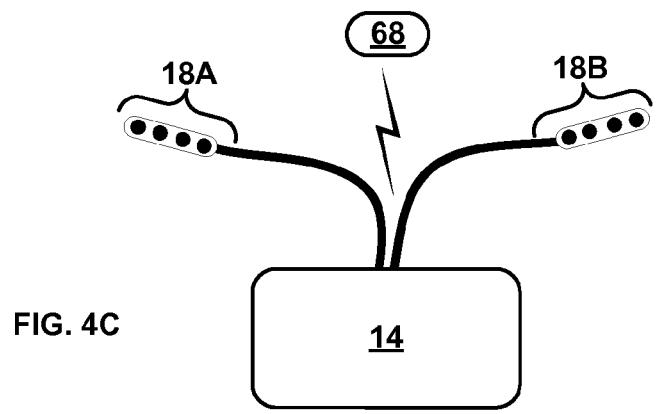

FIGS. 4A-4C and 5A-5B illustrate exemplary configurations of therapy systems in which sensing elements are configured to be anchored to the skull of patient 12 to facilitate determination of the head position of patient 12. FIGS. 4A-4C refer to sensing elements 60, 64, and 68, which represent examples of sensing element 20 and are configured to provide anchored reference points to facilitate determination of the proximity of the sensing elements to another component of the therapy system.

Sensing elements 60, 64, and 68 may be anchored to the skull or another fixed portion of patient 12 using any suitable technique, such as a screw, adhesive (e.g., a medical adhesive), or the like. For example, in some examples, sensing elements 60, 64, and 68 may be anchored to the periosteum of one or more bones, e.g., one or more bones of the skull, of patient 12 using staples or sutures. In some examples, sensing elements 60, 64, and 68 may be incorporated into a bone screw, which may be positioned in the skull via an incision. In other examples, sensing elements 60, 64, and 68 may be configured such that one or more bone screws may pass through a portion of the sensing element to fix the sensing element to the skull at a selected location. In some examples, sensing elements 60, 64, and 68 may be anchored by exposing a portion of the skull of patient 12 through an incision. In some cases, medical adhesive may be used instead of or in addition to the one or more bone screws in order to fixate the sensing elements to the skull. In other examples, sensing elements 60, 64, and 68 may have relatively small dimensions such that sensing elements 60, 64, and 68 may be passed through a needle or otherwise injected into patient 12 to be anchored to the skull of patient 12, which may not require an incision.

FIG. 4A illustrates an exemplary therapy system that includes two sensing elements 60A and 60B (collectively "sensing elements 60") coupled to leads 16A and 16B, respectively. In the example illustrated in FIG. 4A, sensing elements 60 are mechanically coupled to leads 16 via tethers 62A and 62B (collectively "tethers 62"), respectively. In some examples, sensing elements 60 may also be electrically coupled to leads 16 via tethers 62. For example, in some examples, tether 62A may include a conductor extending between one sensing element 60A and lead 16A within tether 62A. In other examples, sensing elements 60 may wirelessly communicate with leads 16 and/or stimulator 14, or the therapy system may include electrical connections between sensing elements 60 and leads 16 and/or stimulator 14 in addition to tethers 62.

Sensing elements 60 may be anchored to any suitable portion of the body of patient 12. For example, each of sensing elements 60 may be anchored to a portion of the skull of patient 12. In some examples, a first sensing element 60 may be anchored to a portion of the skull of patient 12 more proximate to electrodes 18A (and the target stimulation site) than a second sensing element 60. In other examples, one or both of sensing elements 60 may be anchored to a portion of the body of patient 12 other than head 13 of patient 12, e.g., a location within torso 24 of patient 12. In some examples, system 10A includes more than two sensing elements 60, which may be coupled to stimulator 14 and/or leads 16 by additional tethers 62.

Tethers 62 may be configured to facilitate changes in the distance between sensing elements 60 and electrodes 18 (or another component of system 10, e.g., stimulator 14). For example, tethers 62 may be configured to provide extra slack such that, upon movement of the head of patient 12 (which may result in movement of electrodes 18), tethers 62 remain intact and do not break. In some examples, tethers 62 may be tunneled through tissue within the head of patient 12 between sensing elements 20 and electrodes 18.

Tethers 62 may be formed from any suitable material. For example, in some examples, tethers 62 may be formed from an insulating shell of polyurethane, silicone, or any other suitable biocompatible material. In some examples, tethers 62 may define one or more lumens through which a metal conductor extends such that tethers 62 electrically couple sensing elements 20 to leads 16. Hence, the conductor may be provided in a polyurethane, silicone or other insulating sheath. The metal conductors may be of low impedance to pass energy efficiently, and may be straight or coiled, e.g., for additional strain relief or stretching capabilities. In some examples, tethers 62 may be formed from an appropriately flexible, bendable, and/or stretchable material to facilitate relatively free movement of tethers 62 within tissue of patient 12.

FIG. 4B illustrates another exemplary therapy system that includes a single sensing element 64 coupled to both of leads 16 via two tethers 66A and 66B. In some examples, a single sensing element 64 establishing a single reference point may require less energy or power for operation than two individual sensing elements 60A and 60B.

FIG. 4C illustrates another exemplary therapy system that includes a single sensing element 68 configured to wirelessly communicate with stimulator 14, as indicated by the lightning bolt in FIG. 4C. In some examples, sensing element 68 may communicate with stimulator 14 via inductive telemetry. In other examples, sensing element 68 may wirelessly communicate with stimulator 14 using another suitable technology such that sensing element 68 may act as a reference point to determine a parameter indicative of the proximity of sensing element 68 and stimulator 14 and/or leads 16.

Although FIGS. 4A-4C illustrate several exemplary configurations for therapy system 10, other configurations are contemplated. For example, system 10 may include any suitable number of sensing elements mechanically and/or electrically coupled to leads 16, electrodes 18, and/or stimulator 14 in any suitable manner, e.g., using wired or wireless connections.

Figure 5A:
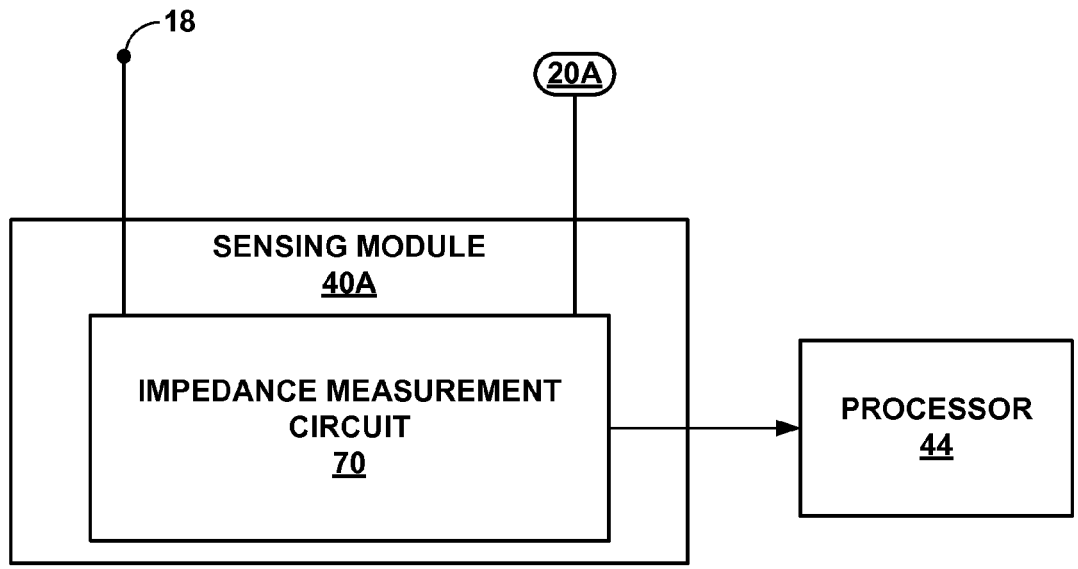
FIGS. 5A-5B are functional block diagrams illustrating exemplary sensing modules coupled to sensing elements of an exemplary therapy system.
Figure 5B:
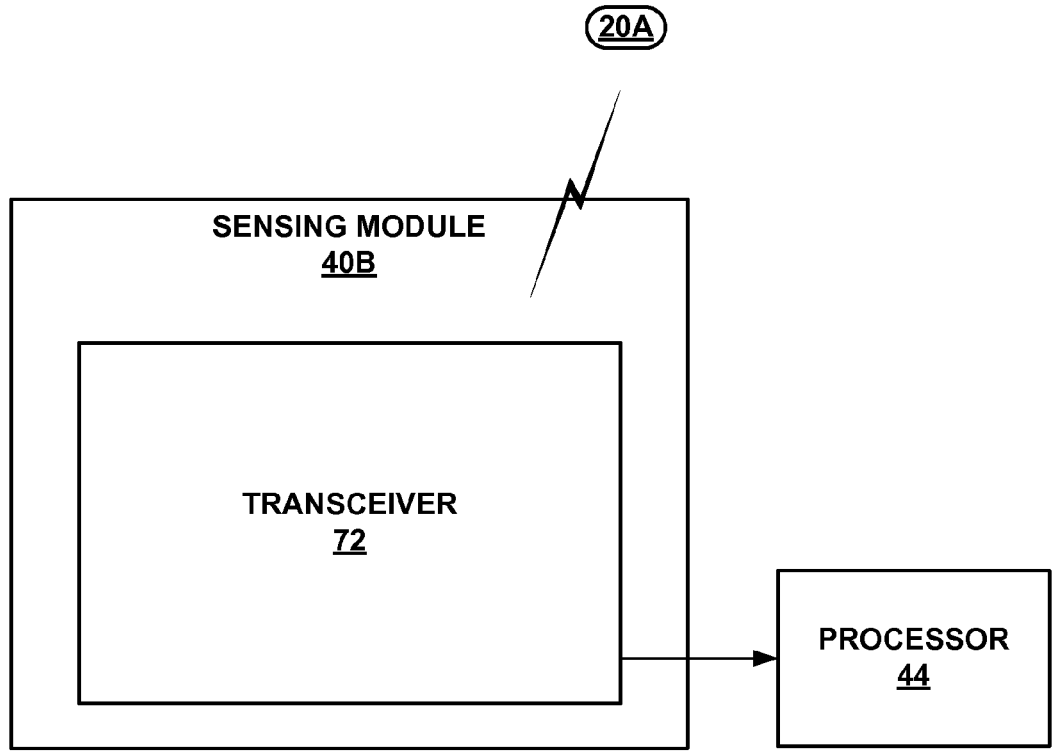

FIGS. 5A and 5B illustrate functional block diagrams associated with exemplary sensing modules 40A and 40B of a therapy system that includes sensing element 20A configured to be anchored to a portion of the body of patient 12 and configured to act as a reference in determining proximity between the sensing element 20A and one or more components of the therapy system. Sensing element 20A illustrated in FIGS. 5A and 5B may represent, among others, any of sensing elements 60, 64, and 68 (FIGS. 4A-4C), which are configured to be anchored to a portion of the body of patient 12.

FIG. 5A illustrates exemplary sensing module 40A that includes impedance measurement circuit 70 configured to measure one or more impedance values between electrode 18 and sensing element 20A, which may be indicative of the head position of patient 12. As described herein, electrode 18 may include any of electrodes 18A and 18B (FIGS. 1-4). In other examples, system 10 may include a separate electrode coupled to impedance measurement circuit 70 for sensing impedance between the electrode and sensing element 20A. In the example illustrated in FIG. 5A, impedance measurement circuit 70 is configured to transmit the measured impedance value(s) to processor 44 such that processor 44 (or another processor of system 10) may determine a head position of patient 12 based on the measured impedance value(s) and subsequently control delivery of electrical stimulation to patient 12 based on the determined head position.

Electrode 18 may be any suitable electrode component coupled to one of leads 16A or 16B such that, when the lead 16 moves, the electrode 18 also moves. As described with respect to FIG. 5A, sensing element 20A is configured to be anchored to the skull of patient 12 and is also configured to act as an electrode. Impedance measurement circuit 70 is configured to measure an impedance value between electrode 18 and sensing element 20A. Because sensing element 20A is anchored to the skull of patient 12 and electrode 18 moves based on the position of lead 16, the impedance of the tissue between sensing element 20A and electrode 18 may change in accordance with movement of lead 16 and the resulting change in distance between sensing element 20A and electrode 18, which may result from the change in head position of patient 12. In this way, impedance of the tissue between sensing element 20A and electrode 18 can be correlated with, i.e., indicative of, the head position of patient 12.

For example, some particular movements of head 13 may cause electrode 18 to move farther away from sensing element 20A, resulting in an increase in the amount of tissue between sensing element 20A and electrode 18 and, consequently, an increase in the impedance of the tissue between sensing element 20A and electrode 18. In examples in which electrode 18 and leads 16 are implanted proximate to occipital nerves of patient 12, movements of head 13, e.g., to the right, to the left, and to the front to varying degrees may result in an increase in the distance between electrode 18 and sensing element 20A.

Similarly, some particular movements of head 13 may cause electrode 18 to move closer to sensing element 20A, resulting in a decrease in the amount of tissue between sensing element 20A and electrode 18 and, consequently, a decrease in the impedance of the tissue between sensing element 20A and electrode 18. In examples in which electrode 18 and leads 16 are implanted proximate to occipital nerves of patient 12, movements of head 13, e.g., to the back may result in a decrease in the distance between electrode 18 and sensing element 20A

In some examples, processor 44 may use impedance to infer distance. In particular, processor 44 may correlate various distances to various impedance measurements based on generally known properties of tissue, such as known impedance per unit distance correlations or known tissue conductivity values. In other examples, processor 44 may utilize a patient-specific correlation between various distances and various impedance measurements of the tissue of patient 12. For example, patient 12 may assume a variety of head positions, impedance measurement circuit 70 may measure impedance for each of the head positions, and processor 44 or another component of system 10 may perform a linear or nonlinear interpolation to determine a relationship between impedance and head position that is specific to patient 12, and which may be used for future reference in controlling stimulation based on head position. In this manner, impedance may be calibrated on a patient-specific basis.

Impedance measurement circuit 70 of sensing module 40A may measure the impedance between electrode 18 and sensing element 20A using any suitable technique. In some examples, impedance measurement circuit 70 may control signal generator 38 to generate an electrical signal and transmit the electrical signal to sensing element 20A (e.g., via one or more conductors extending through one or more tethers coupling sensing element 20A to one of leads 16) and/or electrode 18 as a measurement current. In other examples, impedance measurement circuit 70 may include a separate signal generator for measuring impedance, and may control generation and delivery of the electrical measurement current signal via the separate signal generator. As an example, the impedance measurement circuit 70 may control the signal generator to maintain the electrical signal at a constant current value, measure the voltage value between the electrode 18 and the sensing element 22A, determine the impedance of the tissue between the electrode 18 and the sensing element 22A based on the voltage and current values, and subsequently transmit the determined impedance value to processor 44 (or another processor of system 10). In other examples, impedance measurement circuit 70 may control the signal generator to apply a fixed voltage between sensing element 22A and electrode 18. Impedance measurement circuit 70 may include a sense resistor of known value such that impedance measurement circuit 70 may calculate the current across the sense resistor and utilize the calculated current and fixed voltage to calculate the impedance of the tissue between sensing element 22A and electrode 18, as a resistance, and subsequently transmit the calculated impedance to processor 44 (or another processor of system 10).

In some examples, the impedance measurement circuit 70 may control delivery of a direct current (DC) measurement current via one or more conductors within the tether coupling sensing element 20A to one of leads 16. In these examples, impedance measurement circuit 70 may subsequently determine tissue impedance between sensing element 20A and electrode 18 by measuring a DC voltage caused by a known current flow between sensing element 20A and electrode 18 to determine the resistance between sensing element 20A and electrode 18. In some examples, the DC voltage may be pulsed and biphasic, which may prevent adverse effects on one or more components of system 10 and/or tissue of patient 12 between sensing element 20A and electrode 18.

In other examples, impedance measurement circuit 70 may control delivery of an alternating current (AC) measurement current and subsequently measure complex impedance between sensing element 20A and electrode 18. In some examples, impedance measurement circuit 70 may apply the AC signal at various frequencies such that the frequency-dependent portion of the complex impedance (due to capacitive and/or inductive components of the impedance measurement circuit 70) may be measured by impedance measurement circuit 70 or another component of system 10. In some examples, impedance measurement circuit 70 may apply the AC signal in periodic bursts to facilitate periodic sensing of impedance values while, in other examples, impedance measurement circuit 70 may apply the AC signal substantially continuously to facilitate substantially continuous sensing of impedance values.

In other examples, impedance measurement circuit 70 may measure the impedance between electrode 18 and sensing element 22A using another suitable technique. For example, impedance measurement circuit 70 may use one or more techniques described in U.S. Patent Application No. 2010/0161007 by King, entitled "IMPEDANCE-BASED STIMULATION ADJUSTMENT," which was filed on Mar. 4, 2010 and is incorporated herein by reference in its entirety. Impedance measurement circuit 70 may include resistors, capacitors, or other known circuitry for sensing a value of one or both of a voltage or current when a measurement signal, such as a measurement current, is delivered by a selected electrode 18 or sensing element 22A, such that the impedance between sensing element 22A and electrode 18 may be measured.

In some examples, impedance measurement circuit 70 may be positioned within a housing of stimulator 14. In other examples, impedance measurement circuit 70 may be positioned within another component of system 10, such as programmer 22.

Processor 44 may determine the head position of patient 12 based on the impedance value and control delivery of electrical stimulation by stimulation generator 38 based on the determined head position. For example, in some examples, processor 44 may access a table or other data structure stored in memory 46 that correlates particular impedance values or ranges of impedance values with particular therapy programs or therapy parameter values (e.g., pulse amplitude, pulse rate, pulse width, electrode combination, and/or electrode polarity), and processor 44 may subsequently select a particular therapy program from the table to define the stimulation delivered via stimulation generator 38 based on the measured impedance value. As described in further detail below with respect to FIG. 11, in some examples, a user may create and store a look-up table or other data structure, prior to delivery of electrical stimulation, that associates each of several head positions of patient 12 with an impedance value or range of values and one or more therapy programs. In other examples, the look-up table or other data structure may be automatically generated, e.g., by processor 44 or another processor of system 10. The look-up table can subsequently be useful in selecting a particular therapy program associated with one or more impedance values measured by impedance measurement circuit 70. The impedance value or range of values associated with various head positions of patient 12 may define the parameter indicative of head position of patient 12 that a processor of system 10 may utilize as a basis for controlling delivery of electrical stimulation therapy to patient 12.

FIG. 5B illustrates exemplary sensing module 40B that includes transceiver 72 configured to transmit and receive signal data related to head position of patient 12. As described with respect to FIG. 5B, transceiver 72 has both transmitting and receiving communication capabilities. In other examples, sensing module 40B may include separate modules or components for transmitting and receiving information. That is, transceiver 72 may define separate receiving and transmitting components, instead of being a single module with both transmitting and receiving capabilities.

In the example illustrated in FIG. 5B, transceiver 72 is configured to transmit a signal outward from sensing module 40B into tissue of patient 12. Transceiver 72 may subsequently receive the same signal or another signal that is modulated based on the distance between sensing element 20A and sensing module 40B or transceiver 72, which processor 44 can use to determine the head position of patient 12. Although FIG. 5B illustrates sensing element 20A and transceiver 72 communicating entirely via wireless communication techniques, in other examples, transceiver 72 and sensing element 20A may communicate via one or more wired connections.

In some examples, the sensing element 20A may be a fixed ferrite core, e.g., fixed to the skull of patient 12, and the inductive coil may be positioned in the tissue plane of lead 16. As the inductive coil, which may be coupled to one of leads 16, moves relative to the fixed ferrite core sensing element, changes in inductance may be detected. In some examples, changes in inductance may be detected in a two-axis manner. For example, changes in inductance may be detected in an x-axis direction and in a y-axis direction.

In some examples, transceiver 72 may be coupled to an inductive coil through which signal generator 38 or another component of system 10 may transmit an electrical signal. The electrical signal travelling through the coil may result in generation of an electromagnetic field within and around the coil. In these examples, sensing element 20A may be a ferromagnetic element that interacts with the electromagnetic field and modulates the electromagnetic field based on the proximity of ferromagnetic element 20A to the inductive coil. In some examples, the coil may be coupled to one of leads 16 such that the coil and the lead 16 share substantially the same location. Consequently, the coil may move in accordance with movement of the lead 16. Thus, one or more properties of the electromagnetic field may indicate the position of lead 16 (or another component to which the coil is coupled) relative to the ferromagnetic element 20A, which may correspond to the head position of patient 12.

In some examples, the inductance of the inductive coil may change based on the proximity of the coil to the ferromagnetic element 20A. The inductance of the inductive coil may be measured using any suitable technique. By measuring changes in the inductance, by, for instance, measuring changes to the response of the coil when driven at a known frequency or when driven by an impulse or step function, a relative distance to the ferromagnetic element may be inferred. Alternately, a coil in the lead may be pulsed with energy, perhaps at a frequency known to cause a reflected response by the ferromagnetic element. In this case, the pulsed energy may cause eddy currents to flow in the ferromagnetic element which themselves cause a distinctive electromagnetic signature. The lead borne coil, following the pulse of energy, is then configured to sense the signature caused in the ferromagnetic element. The relative strength of this signature response may then be used to infer the distance between the coil and the element. To enhance the response, the ferromagnetic element may be complemented with or replaced by passive elements such as inductors, capacitors, and resistors such that a resonant tank circuit is formed.

For example, processor 44 or another component of system 10 may control signal generator 38 to generate and deliver a signal defined by a known frequency or an impulse or step function through the inductive coil. Transceiver 72 may subsequently receive a signal indicative of the response of the inductive coil to the delivered signal, which varies based on the proximity to the ferromagnetic element 20A, and processor 44 may determine the inductance of the inductive coil based on the received signal. Processor 44 may subsequently determine the distance between the inductive coil and the ferromagnetic sensing element 20A.

As another example, processor 44 may detect the strength of an electromagnetic signature that processor 44 may correlate to a distance between ferromagnetic sensing element 20A and the inductive coil coupled to lead 16. For example, signal generator 38 may pulse the inductive coil with energy at a frequency known to generate a particular electromagnetic signature response in the ferromagnetic sensing element 20A. The pulsed energy may generate eddy currents within the ferromagnetic sensing element 20A, which may cause the distinct electromagnetic signature. As a result of the pulse of energy delivered through the inductive coil, the inductive coil senses the distinct electromagnetic signature of the ferromagnetic element 20A. Based on the strength of the signature sensed in the inductive coil, processor 44 may determine the distance between the ferromagnetic sensing element 20A and the inductive coil.

In some examples, changes in the properties of the electromagnetic field may result in changes in properties of the electrical signal that travels through the inductive coil. For example, if the inductive coil and the ferromagnetic element 20A are positioned farther from one another, the electrical signal may exhibit a lower strength or smaller change in a property of the coil, e.g., inductance of the coil. Similarly, if the inductive coil and the ferromagnetic element 20A are positioned closer to one another, the electrical signal may exhibit a higher strength or a larger change in a property of the coil, e.g., inductance.

Ferromagnetic element 20A may be formed from any material suitable for interacting with the electromagnetic field generated within the inductive coil. For example, in some examples, ferromagnetic element 20A may be a solid object formed at least in part from iron or another metal material. In other examples, ferromagnetic element 20A may be formed from one or more alloys configured to have high magnetic permeability, e.g., nickel-iron alloys or mu-metals.

As another example, sensing element 20A may include circuitry for receiving and transmitting electrical signals in a manner that is indicative of the proximity of sensing element 20A to transceiver 72. For example, transceiver 72 may generate and transmit an electrical signal defined by a first set of parameters to sensing element 20A. Sensing element 20A may receive the electrical signal from transceiver 72 and subsequently transmit an electrical signal back to transceiver 72. The signal received from sensing element 20A by transceiver 72 may be defined by a second set of parameters, modulated from the first set of parameters. The particular differences between the first set of parameters and the second set of parameters may correlate to the distance between sensing element 20A and transceiver 72, and processor 44 may determine the head position of patient 12, and whether the head position of patient 12 has changed, based on the parameters. In these examples, transceiver 72 may be located on one of leads 16 such that the position of transceiver 72 may be indicative of the position of the lead 16 to which transceiver 72 is coupled, and may be coupled to sensing module 40, e.g., via lead 16.

As a particular example, sensing element 20A may include a resistor-inductor-capacitor (RLC) circuit that acts as a harmonic oscillator for current transmitted through the circuit. The RLC circuit may be configured to resonate at a known resonant frequency, e.g., as defined by $1/(2\pi\sqrt{(LC)})$, upon delivery of external energy through the circuit. The circuit may be designed such that the inductance is provided by a coil configured as an antenna optimized to collect energy transmitted from the transceiver 72. Alternately, such an antenna may be included in addition to the passive elements of the RLC circuit. Thus, transceiver 72 may transmit an electrical signal to sensing element 20A at the resonant frequency of the RLC circuit to energize the circuit. Sensing element 20A may resonate and transmit an electrical signal back to transceiver 72 and, based on the amplitude of the return signal, processor 44 may determine the distance between sensing element 20A and transceiver 72. In some examples, the inductor or inductive coil of the RLC circuit of sensing element 20A may additionally be configured to act as antenna that receives the signal transmitted by transceiver 72. In other examples, sensing element 20A may include a separate inductor or inductive coil that acts as the antenna, in addition to the passive elements of the RLC circuit.

In some examples, transceiver 72 may transmit the electrical signal to sensing element 20A for a period of time. Subsequently, transceiver 72 may terminate transmission of the electrical signal for a period of time such that transceiver 72 may detect the electrical signal resonating at the resonant frequency, e.g., during a "listening" period, and receive the electrical signal back from sensing element 20A. Energy transmitted via the electrical signal to the RLC circuit may cause the RLC circuit to resonate at its resonant frequency, and the antenna of the sensing element 20A may cause the resonance to be transmitted via the antenna as a magnetic and/or electric field such that transceiver 72 may receive the resonance or a signal indicative of the resonance. The strength of the magnetic and/or electric field transmitted from the RLC circuit to the transceiver 72 may decay as a function of distance between the sensing element 20A and the transceiver 72 and, consequently, may be indicative of the proximity of the sensing element 20A to the transceiver 72. Processor 44 may subsequently determine the distance between sensing element 20A and transceiver 72 based on the received electrical signal, e.g., based on an amplitude defining the received electrical signal.

In some examples, transceiver 72 may include multiple sensing coils or antennas coupled to lead 16. Determining the distance between sensing element 20A and multiple sensing coils or antennas may, in some examples, provide information related to the direction of movement of lead 16 relative to the target stimulation site or of the target stimulation site relative to lead 16. For example, if the sensing element 20A including the RLC circuit is positioned relative to transceiver 72 between two adjacent sensing coils or antennas, movement closer to or farther from one of the two adjacent sensing coils may be determined based on the change in strength of the electrical signal sensed by each of the two adjacent sensing coils. For example, if the lead 16 moves such that the transceiver 72 moves farther from the first sensing coil and closer to the second sensing coil, the strength of the signal received by the first sensing coil may decrease and the strength of the signal received by the second sensing coil may increase.

In other examples, sensing element 20A may be formed from a ferrite material, e.g., a ferrite screw. Transceiver 72, which may be coupled to lead 16, may include a Hall effect sensor that may detect changes in distance between the lead and the ferrite sensing element 20A. In some examples, the Hall effect sensor produces various output voltages in response to changes in a magnetic field resulting from proximity to the ferrite sensing element 20A, and the output voltages can be correlated to the distance between sensing element 20A and lead 16.

As another example, sensing element 20A may be a reflective sensing element, and transceiver 72 may transmit an optical signal, e.g., a light signal, to sensing element 20A via an optical signal generator of system 10. Transceiver 72 or a portion of transceiver 72 may be positioned on or coupled to lead 16 such that the position of transceiver 72 correlates to the position of lead 16. The transceiver 72 may also include an optical sensor configured to sense light reflected back from reflective sensor 20A. Processor 44 or another component of system 10 may correlate the amount of light reflected back from reflective sensing element 20A with the amount of tissue between sensing element 20A and transceiver 72 and, consequently, with the proximity of sensing element 20A with transceiver 72. Reflective sensing element 20A may be formed from any suitable selectively reflective material.

In some examples, a processor of system 10, e.g., processor 44 or processor 50, may determine the head position or a parameter indicative of head position of patient 12 based on an electrical signal indicative of motion and/or position of patient 12, instead of or in addition to determining the head position of patient 12 based on a parameter indicative of the proximity of sensing element 20 to a component of system 10. For example, sensing element 20 may include a motion and/or position sensor, such as one or more single and/or multi-axis accelerometers, e.g., one or more microelectromechanical accelerometers, that can generate a signal indicative of the motion or position of a portion of the body of patient 12 within which the sensing element 20 is implanted. The one or more accelerometers may include single-axis, two-axis, or three-axis accelerometers, which may be capable of detecting static orientation or vectors in three-dimensions. In some examples, an accelerometer may measure changes in acceleration along one or more axes. In other examples, sensing element 20 may include one or more gyroscopes, pressure transducers, piezoelectric crystals, or other sensors that generate a signal indicative of patient motion and/or position.

In some examples, the processor may utilize velocity and acceleration of head 13 of patient 12 (e.g., as indicated by a signal indicative of motion and/or position generated by sensing element 20) in determining the parameter indicative of head position of patient 12 and in subsequently controlling the delivery of electrical stimulation based on the determined parameter. For example, in some examples, a relatively rapid movement of head 13 from a first position to a second position may result in relatively abrupt or rapid changes in the electrical stimulation that may be perceived by patient 12 as, e.g., a jolt or a shock. In these examples, a relatively slow movement of head 13 from the first position to the second position may not result in such abrupt or rapid changes in therapy. Thus, the processor may control delivery of electrical stimulation, e.g., adjust one or more parameters defining the electrical stimulation, differently based on the velocity or acceleration of the head 13 of patient 12, in addition to the position of head 13.

FIGS. 6A-6D, 7, and 8 illustrate exemplary configurations of therapy systems in which one or more sensing elements are configured to sense an electrical signal indicative of motion and/or position of a portion of the body of patient 12. In some examples, the sensing elements may be positioned within the head of patient 12 to directly sense the position of the head of patient 12 and/or to directly sense the motion of the head of patient 12.

FIGS. 6A-6D refer to sensing elements 74, 76, 78, and 80, which represent examples of sensing element 20 and are configured to generate electrical signals indicative of motion and/or position of the portion of patient 12 within which sensing elements 74, 76, 78, and 80 are implanted.

Figure 6B:
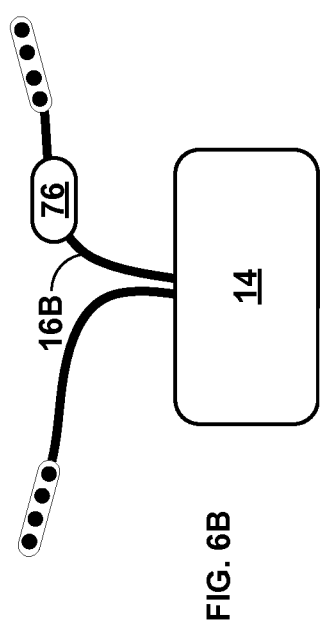
FIGS. 6A-6D are conceptual diagrams illustrating example configurations for therapy systems that include one or more sensing elements configured to generate an electrical signal indicative of motion and/or position of a portion of the body of a patient.
Figure 6D:
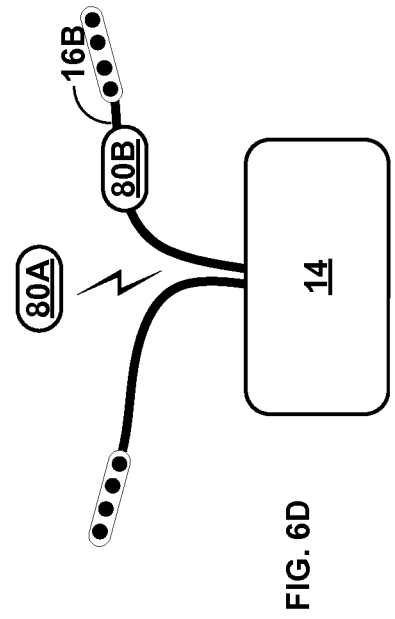
Figure 6A:
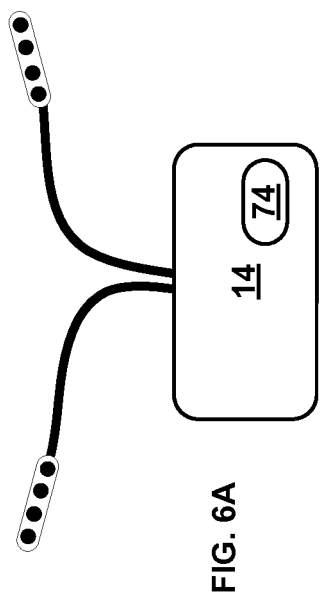

FIG. 6A illustrates an exemplary therapy system that includes sensing element 74 positioned on or coupled to the housing of stimulator 14. In examples in which stimulator 14 is positioned within the head or neck of patient 12, e.g., as illustrated in FIG. 1A, sensing element 74 coupled to stimulator 14 may directly sense the motion and/or position of the head or neck of patient 12. In other examples, sensing element 74 may sense the motion or position of a different portion of the body of patient 12.

Sensing element 74 may be coupled to a housing of stimulator 14 in any suitable manner. For example, in some examples, sensing element 74 may be coupled to the housing via an adhesive, such as, e.g., an epoxy adhesive. In other examples, sensing element 74 may be formed as an integral component of the housing of stimulator 14.

FIG. 6B illustrates an exemplary therapy system that includes sensing element 76 coupled to lead 16B. Sensing element 76 coupled to lead 16B is configured to sense motion and/or position of lead 16B. In examples in which lead 16B is implanted within the head of patient 12, e.g., proximate to one or more occipital nerves of patient 12, the motion of lead 16B may correlate to the head position of patient 12. Thus, a signal generated by sensing element 76 indicative of the motion and/or position of lead 16B may provide information about the motion and/or position of the head of patient 12.

Figure 6C:
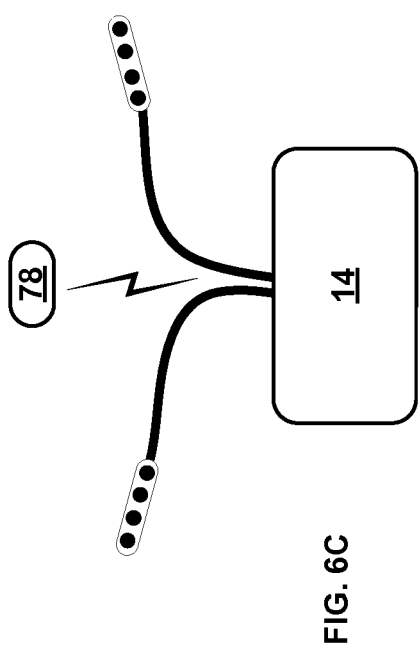

FIG. 6C illustrates an exemplary therapy system that includes sensing element 78 configured to wirelessly communicate with stimulator 14. Sensing element 78 may be positioned within various portions of the body of patient 14. For example, sensing element 78 may be positioned within the head of patient 12 to generate a signal indicative of the motion and/or position of the head of patient 12. Sensing element 78 may be configured to transmit the signal indicative of motion and/or position of the head of patient 12 to stimulator 14 via any suitable wireless communications techniques.

FIG. 6D illustrates an exemplary therapy system that includes two sensing elements 80A and 80B (collectively "sensing elements 80"). Sensing element 80A is configured to be implanted remote from stimulator 14 and sensing element 80B is coupled to lead 16B. In some examples, a therapy system including two sensing elements 80 that sense motion and/or position may provide confirmation about movement and/or position of the head of patient 12. For example, an electrical signal generated by the first sensing element 80A may be compared to an electrical signal generated by the second sensing element 80B to confirm that the first electrical signal accurately indicates the head position of patient 12.

Figure 7:
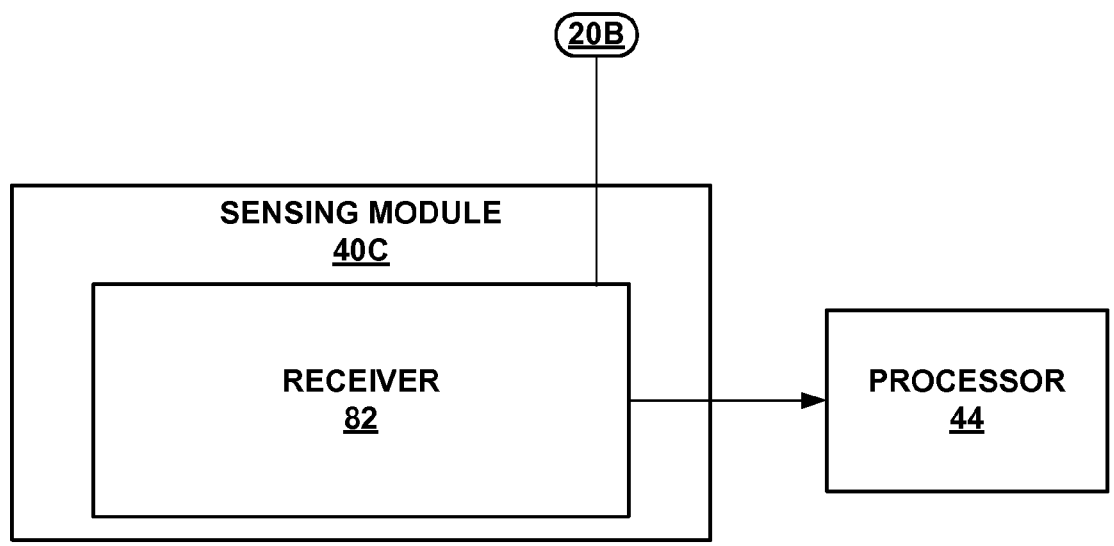
FIG. 7 is a functional block diagram illustrating an exemplary sensing module coupled to a sensing element configured to sense motion and/or position of a portion of the body of a patient.

FIG. 7 illustrates a functional block diagram associated with exemplary sensing module 40C of a therapy system that includes sensing element 20B configured to receive an electrical signal indicative of motion and/or position of a portion of the body of patient 12 from sensing element 20B. Sensing element 20B illustrated in FIG. 7 may represent, among others, any of sensing element 74, 76, 78, and 80 (FIGS. 6A-6D), which are configured to generate an electrical signal indicative of motion and/or position of the portion of the body of patient 12 within which sensing element 74, 76, 78, or 80 is implanted.

As discussed previously, in some examples, sensing element 20B may include accelerometers, gyroscopes, pressure transducers, piezoelectric crystals, or other sensors that generate an electrical signal indicative of motion and/or position of a portion of the body of patient 12. In the example illustrated in FIG. 7, receiver 82 of sensing module 40C is configured to receive an electrical signal from sensing element 20B. The electrical signal generated by sensing element 20B may provide information about the position or change of position of sensing element 20B in space. For example, sensing element 20B may be a gyroscope which provides electrical signals indicative of the absolute position of sensing element 20B in x, y, and z-axis directions, or an accelerometer which provides electrical signals indicative of the change in position of sensing element 20B in x, y, and z-axis directions. The position or change in position of sensing element 20B may correspond to the position or change in position of the head of patient 12 and, consequently, may be useful in determining head position of patient 12.

In addition, receiver 82 may also be configured to communicate with processor 44, or another processor of therapy system 10, to transmit information related to the electrical signal to processor 44. For example, receiver 82 may transmit the raw electrical signal position/motion data received from sensing element 20B to processor 44. In other examples, receiver 82 may perform some extraction of particular data from the electrical signal data, such extraction of particular parameter values (e.g., amplitude values) or particular types of data (e.g., only x-axis data, only y-axis data, or only z-axis data) that may be useful to processor 44 in determining head position.

Processor 44 may subsequently analyze the information received from receiver 82 to determine a parameter indicative of a head position of patient 12. For example, processor 44 may, in some examples, compare one or more characteristics defining the electrical signal data to one or more values or ranges of values stored in a table in memory 46, where the one or more values or ranges of values stored in the table corresponds to particular head positions of patient 12. In other examples, processor 44 may utilize other techniques to determine the parameter indicative of head position of patient 12. For example, processor 44 may access and execute one or more algorithms that utilizes the electrical signal data to generate a parameter indicative of the head position of patient 12, e.g., a value of one or more characteristics defining the electrical signal that corresponds to a particular head position of patient 12.

As described with respect to FIG. 7, sensing element 20B is configured to be positioned within the head of patient 12 to directly sense motion and/or position of the head of patient 12, which may be correlated to movement of one or both of leads 16 implanted within the head 13 or neck 15 of patient 12. However, in other examples, sensing element 20B may be positioned in any portion of the body of patient 12 such that the motion and/or position data sensed by sensing element 20B may be related to and facilitate determination of head position of patient 12. For example, in some examples, as described with respect to FIG. 8, therapy system 10 may include a sensing element 20B implanted within the torso 24 of patient 12 to generate an electrical signal indicative of motion and/or position of the torso 24 of patient 12.

As previously mentioned, in some examples, system 10 may include two sensing elements 20B which may generate first and second electrical signals that may be compared to one another to confirm that the first electrical signal accurately indicates the head position of patient 12. For example, the first sensing element 20B may be positioned within the head 13 of patient 12 proximate to lead 16 and the second sensing element 20B may be positioned within the head 13 of patient 12 remote from the lead 16 proximate to which the first sensing element 20B is positioned. Processor 44 or another processor of system 10 may compare one or more properties, e.g., one or more amplitude values, frequency values, pulse width values, and the like, of the first and second electrical signals generated by the first and second sensing elements 20B to one another to determine whether the head position that corresponds to each of the electrical signals is the same. If the head position is the same, processor 44 may determine that the electrical signal generated by the first sensing element 20B is accurately indicating the head position of patient 12. If, on the other hand, the corresponding head position is different, processor 44 may determine that either the first or second electrical signals does not accurately indicate the head position of patient 12.

Figure 8:
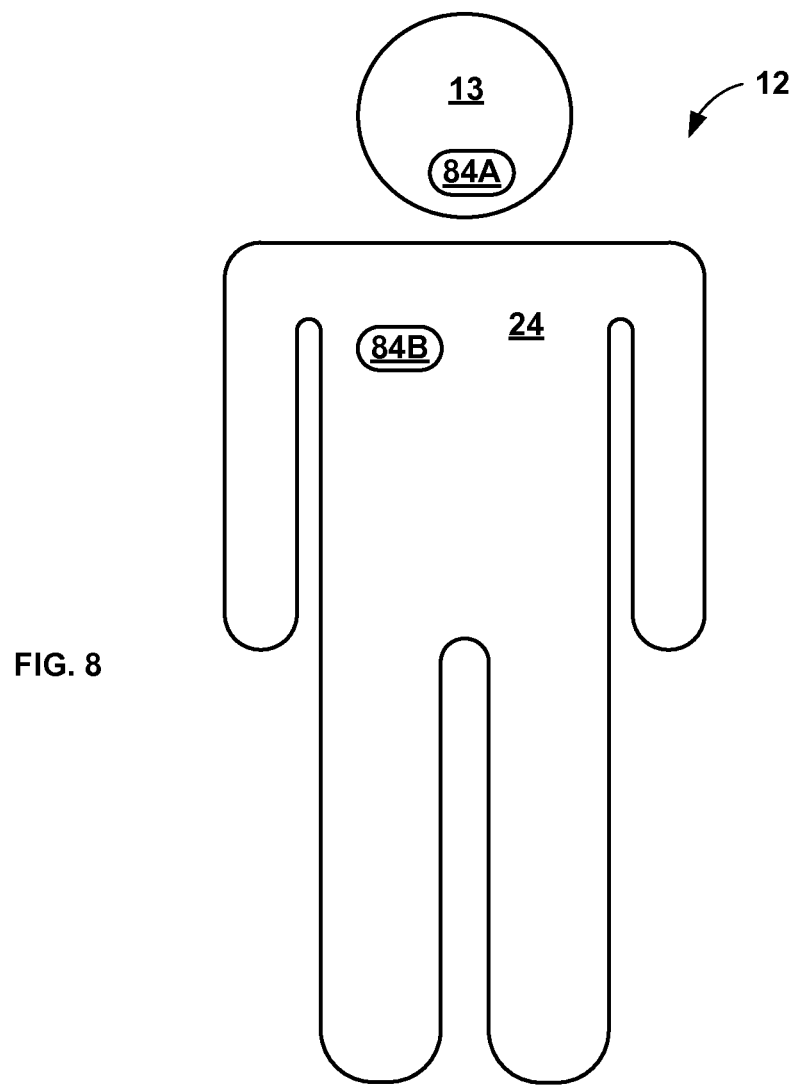
FIG. 8 is a diagram illustrating a therapy system that includes a first sensing element configured to sense motion and/or position of the head of a patient and a second sensing element configured to sense motion and/or position of the torso of the patient.

FIG. 8 is a schematic diagram illustrating two sensing elements 84A and 84B (collectively "sensing elements 84") implanted within patient 12. In particular, in the example illustrated in FIG. 8, sensing element 84A is implanted within head 13 of patient 12 and sensing element 84B is implanted within torso 24 of patient 12. Sensing elements 84A and 84B represent examples of sensing element 20B (FIG. 7), which is configured to generate an electrical signal indicative of motion and/or position of the portion of the body within which the sensing element is implanted.

Sensing element 84A positioned within the head 13 of patient 12 is configured to generate an electrical signal indicative of the position and/or motion of head 13. Similarly, sensing element 84B positioned within torso 24 of patient 12 is configured to generate an electrical signal indicative of the position and/or motion of torso 24. In some examples, a configuration including both sensing element 84A and sensing element 84B may be useful in determining whether head 13 of patient 12 has moved relative to torso 24 of patient 12. For example, the electrical signals generated by sensing element 84A and sensing element 84B may be compared to one another to determine whether patient 12 has moved head 13 alone or has rotated both head 13 and torso 24 in the same direction.

In some examples, if patient 12 fully rotates his or her body in a particular direction (e.g., rotates both head 13 and torso 24 in the same direction), leads 16 may not move within head 13 of patient 12 with respect to the target stimulation site. That is, movement of the entire body of patient 12 in a particular direction may not result in movement of the leads 16 within head 13 of patient 12. Instead, movement of the leads 16 within head 13 may only occur if patient 12 moves head 13 separately from the rest of the body.

In some examples, in order to determine whether patient 12 has moved head 13 relative to the rest of the body, e.g., including torso 24, processor 44 may compare the electrical signals generated by sensing elements 84A and 84B. If processor 44 determines that patient 12 has moved head 13 relative to the rest of the body, then processor 44 may proceed to determining the head position of patient 12, e.g., using any of the exemplary therapy systems described previously. In this way, a therapy system that includes both sensing elements 84A and 84B may more accurately detect times in which movement of lead 16 is probable.

Although the examples described herein primarily refer to leads 16 implanted proximate to occipital nerves of patient 12, in other examples, leads 16 may be implanted proximate to other portions of the body of patient 12. In some examples, movement of head 13 may affect the efficacy of therapy delivery to other portions of the body of patient 12. For example, in examples in which leads 16 are implanted proximate to the spinal cord of patient 12, movement of the head 13 may result in movement of the spinal cord, which may cause the target stimulation site on the spinal cord to move relative to particular portions of the lead 16 and particular electrodes 18. In some examples, movement of head 13 forward and backward, for example, may result in movement of the spinal cord up and down, thus resulting in movement of the target stimulation site on the spinal cord relative to particular electrodes. As another example, leads 16 implanted in the cervical region of the spine, e.g., within the neck 15 of patient 12, may, in some examples, experience forces and, consequently, motion relative to the target stimulation site when one or more muscles of the neck 15 of patient 12 are engaged to move head 13. In these examples, head position may serve as an indirect correlate of the motion of the spinal cord relative to the substantially fixed location of the leads in the epidural space. This correlation can be used as an indirect signal to change parameters of stimulation to those more favorable to the new head position.

As a result, in some examples, processor 44 may determine a parameter that corresponds to the head position of patient 12 and may control delivery of electrical stimulation therapy to the spinal cord based on the determined head position by, e.g., adjusting one or more parameters defining the spinal stimulation or selecting different therapy programs that define the spinal stimulation. For example, in examples in which motion of head 13 forward and backward results in movement of the spinal cord of patient 12 rostral and caudal, respectively, with respect to one or more fixed leads 16 implanted along the spinal cord, processor 44 may be configured to shift delivery of electrical stimulation to engage more rostral electrodes 18 of lead 16 or more caudal electrodes 18 of lead 16, respectively. As another example, in some examples, the spinal cord of patient 12 may rotate based on movement of head 13, e.g., rotation of head 13. In these examples, processor 44 may be configured to shift delivery of electrical stimulation to engage more medial or more lateral stimulation by, e.g., engaging more medial or more lateral electrodes 18 or by adjusting the strength of the electrical stimulation in accordance with the sensed degree of rotation of head 13. In some examples, processor 44 may utilize a combination of head position and head rotation to shift stimulation rostrally or caudally, and medially or laterally, substantially simultaneously, which may also require processor 44 to adjust stimulation intensity or other parameters defining the electrical stimulation.

Hence, combinations of head position and rotation may be used to shift stimulation both rostral/caudal and medial/lateral at the same time. Such compound shifts may further require change to delivered stimulation intensity or other parameters as well. Such changes may be continuously variable, shifting from a first set of parameters to a second as the head position is sensed to be moving from a first position/orientation to a second. Alternately, such changes may change discretely, based on determination that the head has assumed one position/orientation of a set of specifically defined position/orientations. These configurations may be created in a clinician environment by asking the patient to assume various combinations of posture and head position and then optimizing stimulation parameters for each. Alternately, the system may be configured to remember the patient's favored settings for each of several defined head positions or posture combinations.

Figure 9:
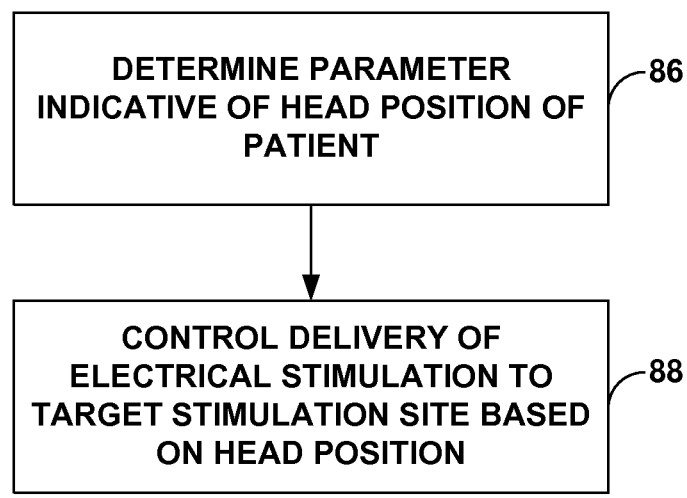
FIG. 9 is a flow diagram illustrating an example technique for controlling delivery of electrical stimulation based on a determined head position of a patient.

FIG. 9 illustrates an example technique that may be performed by processor 44 to control delivery of therapy based on head position of patient 12. While FIG. 9 is described as being performed by processor 44, in other examples, a processor of another device described herein, e.g., processor 50 of programmer 22, may additionally or alternatively perform any part of the technique shown in FIG. 9 alone or with the aid of a user.

In accordance with the technique illustrated in FIG. 9, processor 44 determines a parameter indicative of the head position of patient 12 (86), using any suitable technique. In some examples, as discussed above, processor 44 may receive an electrical signal from sensing element 20 and sensing module 40 that is indicative of the head position of patient 12. For example, as discussed above, processor 44 may receive a signal indicative of impedance of tissue of patient 12 that correlates to the distance between sensing element 20 and another component of patient 12 and that is indicative of the head position of patient 12. As another example, as discussed above, processor 44 may receive an electrical signal indicative of modulation of an electromagnetic field generated by an inductive coil, e.g., coupled to one of leads 16. The modulations of the electromagnetic field may be reflected in the electrical signal generated within the inductive coil, and may be indicative of the distance between sensing element 20 and the inductive coil. As another example, as discussed above, processor 44 may receive a signal that is directly indicative of motion and/or position of the head of patient 12, e.g., an electrical signal generated by an accelerometer or a gyroscope. Processor 44 may determine the parameter indicative of the head position of patient 12 based on one or more characteristics defining the electrical signal.

Upon determining the parameter indicative of head position of patient 12, processor 44 controls delivery of electrical stimulation to the target stimulation site based on the determined parameter indicative of head position (88). In some examples, depending upon the determined parameter indicative of head position, processor 44 may control delivery of electrical stimulation by adjusting, e.g., increasing or decreasing, one or more parameters defining the electrical stimulation. In other examples, processor 44 may substantially entirely deactivate delivery of the electrical stimulation to the target stimulation site based on the determined parameter indicative of head position. In yet other examples, processor 44 may select one or more different therapy programs defining the electrical stimulation based on the determined parameter indicative of head position.

Processor 44 controls delivery of electrical stimulation to the target stimulation site in order to deliver the most efficacious stimulation possible to treat the disorder of patient 12, based on the head position of patient 12 which may correlate to the position of leads 16 relative to the target stimulation site. In some examples, processor 44 may access a table or other data structure stored in a memory of therapy system 10, e.g., memory 46, that associates various parameter values or ranges of parameter values with particular stimulation therapy programs or with particular parameters defining a currently applied therapy program, in order to select a set of stimulation parameters for delivery to the target stimulation site based on the head position.

For example, as discussed previously, e.g., with respect to FIGS. 4 and 5, sensing module 40 may receive an electrical signal that indicates the impedance between sensing element 20 and an electrode, which may correspond to the distance between the sensing element 20 and the electrode, thus correlating to the head position of patient 12 or movement in the head position of patient 12. In these examples, processor 44 may access a table stored in a memory of therapy system 10 that associates various impedance values or ranges of impedance values with particular stimulation therapy programs or therapy parameters that were previously determined to be efficacious for head positions of patient 12 associated with the measured impedance values. Processor 44 may subsequently implement the stimulation therapy programs or therapy parameters selected from the table. In other examples, processor 44 may control delivery of stimulation to the target tissue site by implementing an algorithm that has been previously created to generate one or more stimulation therapy programs based on one or more input parameters, e.g., impedance, indicative of head position of patient 12.

Figure 10:
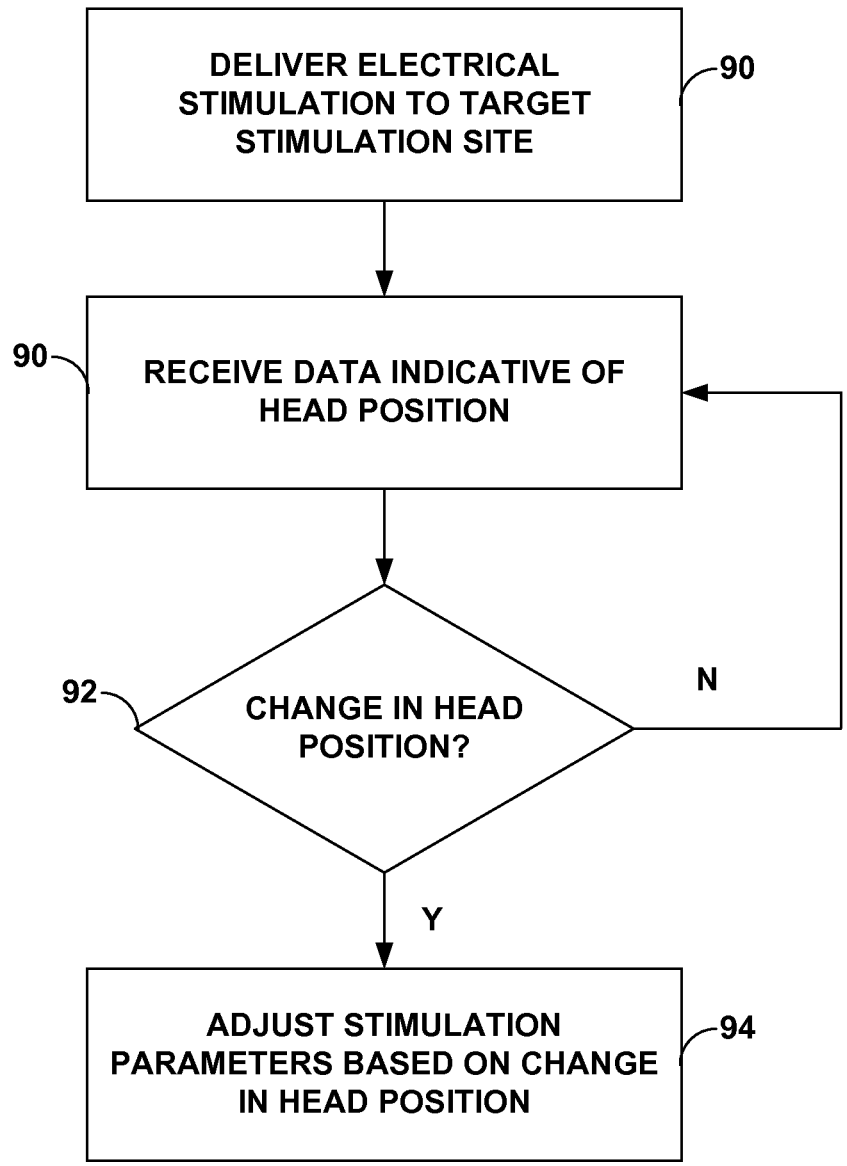
FIG. 10 is a flow diagram illustrating an example technique for adjusting stimulation parameters based on detecting a change in head position of a patient.

FIG. 10 illustrates an example technique that may be performed by processor 44 to adjust stimulation parameters based on a change in head position of patient 12. In some examples, as discussed above, a change in the head position of patient 12 may result in movement of one or more of leads 16 relative to a target stimulation site, which may modify the efficacy and efficiency of the electrical stimulation delivered to the target stimulation site. Thus, adjusting stimulation parameters based on a change in head position may be helpful in reestablishing the efficacy and efficiency of the electrical stimulation therapy. While FIG. 10 is described as being performed by processor 44, in other examples, a processor of another device described herein, e.g., processor 50 of programmer 22, may additionally or alternatively perform any part of the technique shown in FIG. 10 alone or with the aid of a user.

According to the technique illustrated in FIG. 10, processor 44 controls stimulation generator 38 to deliver electrical stimulation to the target stimulation site within patient 12 (90). The electrical stimulation may be defined by particular amplitude values, frequency values, pulse width values, electrode combinations, and the like. Processor 44 may subsequently receive electrical signal data indicative of the head position of patient 12 (90). Upon receiving the electrical signal data, processor 44 may analyze the data, using any suitable technique, to determine whether the head position of patient 12 has changed (92). For example, processor 44 may analyze the signal data to determine whether the value of a parameter indicative of head position of patient 12 has changed over time. In some examples, the value may be an impedance value derived from the electrical signal, an inductance value derived from the electrical signal, a value indicative of the strength (e.g., energy) of the electrical signal, or one or more amplitude, frequency, or pulse width values defining the electrical signal.

If processor 44 does not detect a change in head position based on the electrical signal data, processor 44 may continue to receive and analyze additional electrical signal data indicative of the head position of patient 12 to determine whether a change in head position has taken place. If, on the other hand, processor 44 does detect a change in head position of patient 12, processor 44 may control stimulation generator 38 to adjust stimulation parameters based on the change in head position (94). For example, processor 44 may control stimulation generator 38 to deliver electrical stimulation defined by different amplitude values, different frequency values, different pulse width values, different electrode combinations, and the like based on detecting the change in head position of the patient 12. Adjusting one or more stimulation parameters in accordance with detecting the change in head position of patient 12 may help to maintain or reestablish the efficacy of the electrical stimulation therapy in treating the disorder of patient 12.

FIG. 11 illustrates an example technique for generating a mapping, such as a table, that associates one or more parameter values (or ranges thereof) indicative of particular head positions of patient 12 with one or more therapy programs or therapy parameter settings. In some examples, the table may be stored within a memory of therapy system 10, e.g., memory 46 or memory 52, such that processor 44, processor 50, or a user may access the table to select one or more therapy programs based on a sensed parameter indicative of head position of patient 12, in order to provide sufficiently efficacious therapy to treat the disorder of patient 12. While FIG. 11 is described as being performed by a component of processor 50 of programmer 22, in other examples, a processor of another device described herein, e.g., processor 44 of stimulator 14, may additionally or alternatively perform any part of the technique shown in FIG. 11 alone or with the aid of a user.

According to the technique illustrated in FIG. 11, processor 50 receives user input indicative of a first head position of patient 12 (96). For example, patient 12 may assume a first head position and a user, e.g., patient 12 or a clinician, may provide input indicating that patient 12 has assumed the first head position. In some examples, the user may provide the input via user interface 56 of programmer 22. Upon receiving the user input indicating that patient 12 has assumed the first head position, processor 50 receives a first parameter value (98) that corresponds to the first head position. For example, processor 50 may receive, e.g., from processor 44 of stimulator 14, the first parameter value sensed by sensing module 40 while patient 12 has assumed the first head position. In some examples, as previously discussed, the parameter value may include one or more impedance values, one or more parameter values defining an accelerometer signal, one or more parameter values defining an electromagnetic field, etc, indicative of the head position of patient 12.

In accordance with the technique illustrated in FIG. 11, processor 50 receives input selecting a first therapy program (100), while patient 12 is assuming the first head position. For example, processor 50 may control stimulator 14 to deliver electrical stimulation defined by several different therapy programs to patient 12 while patient 12 is assuming the first head position, and patient 12 or another user (e.g., a clinician) may provide input selecting one or more of therapy programs that is most efficacious in treating the disorder of patient 12 while patient 12 is in the first head position. Upon receiving input selecting the first therapy program, processor 50 generates a table associating the first parameter value, indicative of the first head position of patient 12, and the first therapy program (102). In some examples, processor 50 stores the table within a memory of system 10, such as memory 46 of stimulator 14 or memory 52 of programmer 22.

Upon creating the table, processor 50 updates the table with additional parameter values and associated therapy programs. As illustrated in FIG. 11, processor 50 subsequently receives user input indicative of a second head position of patient 12 (104). For example, processor 50 may again receive input from, e.g., patient 12 or a clinician, via user interface 56 indicating that patient 12 has assumed a second head position, e.g., a head position different than the first head position. Processor 50 may subsequently receive a second parameter value (106), e.g., from processor 44, that corresponds to the second head position. Processor 50 may subsequently receive input selecting a second therapy program (108) to be associated with the second head position and second parameter value. Patient 12 or another user may provide input selecting the second therapy program, which indicates that the second therapy program may be efficacious in treating the disorder of patient 12 while patient 12 is assuming the second head position. Upon receiving input selecting the second therapy program, processor 50 updates the table to associate the second parameter value with the second therapy program (110). For example, processor 50 may access the table stored in one of the memories of system 10, and add another subset of information associating the second parameter value with the second therapy program.

Table 1 illustrates an exemplary table that associates ranges of sensed parameters indicative of head position of patient 12 with sets of stimulation settings, e.g., a table that may be created by a processor 50 using the technique illustrated in FIG. 11. In the example below, the numbers included in the table defining the particular stimulation settings, e.g., 1, 2, 3, 4, and 5, may not denote actual values. Instead, each of the numbers 1, 2, 3, 4, 5, and so on may correspond to an actual value defining the particular stimulation setting. For example, amplitude 1 may correspond to electrical stimulation defined by an amplitude value of approximately 1 milliAmp (mA), which may have been previously determined to provide efficacious therapy when the parameter indicative of head position of patient 12 falls within the range X1-X2.

In some examples, the parameter ranges included in Table 1 may be representative of ranges of values of a parameter indicative of head position of patient 12. For example, in some examples, the parameter may be impedance, and the parameter ranges may be ranges of impedance values. If a sensed impedance value falls within a particular range of values, e.g., within X1-X2, processor 50 may control stimulation generator 38 to deliver electrical stimulation therapy defined by the stimulation settings corresponding to the particular range of values, e.g., program 1, amplitude 1, pulse width 1, pulse rate 1, and electrode configuration 1.

TABLE 1

Exemplary table associating ranges of sensed parameter values and therapy parameter settings

| Sensed Parameter Range | Stimulation Settings | | | | |
|---|---|---|---|---|---|
| | Program | Amplitude | Pulse Width | Pulse Rate | Electrode Configuration |
| X1-X2 | 1 | 1 | 1 | 1 | 1 |
| X2-X3 | 1 | 2 | 1 | 2 | 1 |
| X3-X4 | 2 | 3 | 3 | 3 | 2 |
| X4-X5 | 2 | 4 | 4 | 4 | 2 |
| . | . | . | . | . | . |
| . | . | . | . | . | . |
| . | . | . | . | . | . |
| Xm-Xn | 3 | 5 | 5 | 5 | 3 |

The intensity of the electrical stimulation delivered via system 10 may be a function of a variety of parameters, such as amplitude, pulse width, and pulse rate, as illustrated in Table 1. In some examples, the intensity of the electrical stimulation received at the target stimulation site may also be dependent upon the particular electrodes, e.g., electrode configuration, through which the electrical stimulation is delivered. For example, in order to decrease intensity of electrical stimulation, processor 50 may select an electrode configuration that includes electrodes positioned further from the target stimulation site. Similarly, in order to increase intensity of electrical stimulation, in some examples, processor 50 may select an electrode configuration that includes electrodes positioned closer to the target stimulation site.

In some examples, instead of implementing a new therapy program, processor 50 may deliver electrical stimulation according to a currently applied therapy program with adjustments to one or more parameter settings of the currently applied therapy program. In addition, in some examples, patient 12 may provide input, e.g., via programmer 22, selecting efficacious therapy programs or therapy parameters that can be associated with particular parameters indicative of head position of patient 12 and used by a processor of system 10 to control delivery of electrical stimulation based on a parameter indicative of head position of patient 12.

In some examples, a processor of system 10, e.g., processor 44, may utilize a table such as Table 1 to interpolate stimulation parameter values that correlate to particular sensed parameters indicative of head position of patient 12. As an example, if the parameter indicative of head position of patient 12 is degree of rotation of head 13, processor 44 may note that, based on values recorded in the table, zero degrees of rotation of head 13 corresponds to stimulation defined by 1.0 mA and 60 degrees of rotation of head 13 corresponds to stimulation defined by 3.0 mA. Thus, processor 44 may subsequently determine that the amplitude defining the electrical stimulation should change by 2.0 mA for every 60 degrees of rotation of head 13, or 1.0 mA for every 30 degrees of rotation. Processor 44 may subsequently utilize this correlation to determine stimulation parameters effective in treating the disorder of patient 12.

Although the technique illustrated in FIG. 11 involves generating a table with two associations between parameter values and therapy programs, in other examples, processor 50 or another processor of system 10 generates a table that includes more than two associations between parameter values and therapy programs. A table that includes more associated parameter values and therapy programs may be advantageous because such a table may provide more options for selecting a particular therapy program than a table with fewer associated parameter values and therapy programs, which may result in therapy parameters that are more specifically tailored to patient 12.

In addition, although the technique illustrated in FIG. 11 involves generating a table with associations between one parameter value and one therapy program, in other examples, the table may comprise associations between a range of parameter values and a particular therapy program. For example, the table generated by processor 50 may associate a range of impedance values with a particular therapy program or particular adjustments to therapy parameter values for a currently-implemented therapy program, instead of associating one particular impedance value with the particular therapy program.

In other examples, a processor of system 10 may shift the electrical stimulation field generated by the selected electrodes in accordance with the direction of movement of head 13 by, for example, shifting and/or changing selected electrodes. In other examples, the processor may use field shaping to shift the field in accordance with the amount of movement of head 13 detected.

Figure 12:
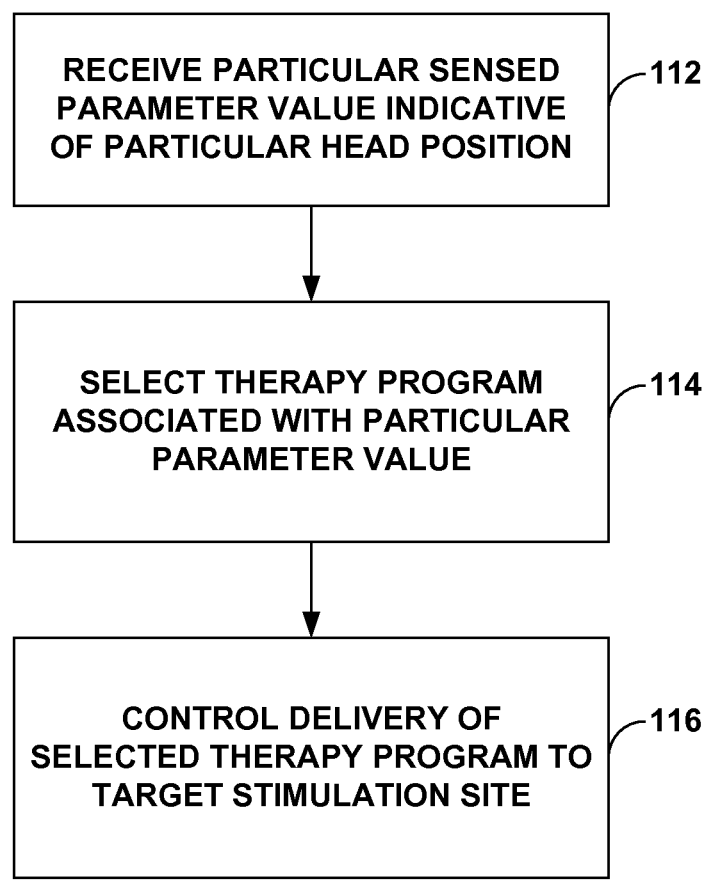
FIG. 12 is a flow diagram illustrating an example technique for controlling delivery of a therapy program to a target stimulation site based on receiving a particular sensed parameter value indicative of a particular head position of a patient.

FIG. 12 illustrates an example technique that may be performed by processor 44 to control stimulator 14 to deliver electrical stimulation to the target stimulation site based on a particular sensed parameter value. While FIG. 12 is described as being performed by processor 44, in other examples, a processor of another device described herein, e.g., processor 50 of programmer 22, may additionally or alternatively perform any part of the technique shown in FIG. 12 alone or with the aid of a user.

In accordance with the technique illustrated in FIG. 12, processor 44 receives a particular sensed parameter value indicative of a particular head position of patient 12 (112). For example, processor 44 may receive a parameter value sensed by sensing module 44, e.g., an impedance value that indicates the head position of patient 12. As discussed previously, the head position of patient 12 may be related to the position of lead 16 with respect to the target stimulation site and, consequently, may affect the efficacy of the therapy delivered via the lead 16 to the target stimulation site.

Upon receiving the particular sensed parameter value indicative of the particular head position of patient 12, processor 44 selects a therapy program associated with the particular parameter value (114). For example, in some examples, processor 44 may access a table that associates parameter values with therapy programs, such as the table discussed with respect to FIG. 11, in order to select a therapy program associated with the sensed parameter value. In other examples, processor 44 may implement an algorithm created to associate parameter values and therapy programs, utilizing the sensed parameter as input for the algorithm and selecting the therapy program that is output by executing the algorithm. In yet other examples, processor 44 may access a table that has been generated over time, e.g., by stimulator 14 or programmer 22, while system 10 functioned in a learning mode, as discussed previously.

Upon selecting the therapy program associated with the sensed parameter value indicative of head position, processor 44 controls delivery of the selected therapy program to the target stimulation site within patient 12 (116). For example, processor 44 may control stimulation generator 38 to deliver electrical stimulation defined by one or more parameters specified in the therapy program, e.g., one or more amplitude values, frequency values, pulse width values, electrode combinations, and the like.

Figure 13:
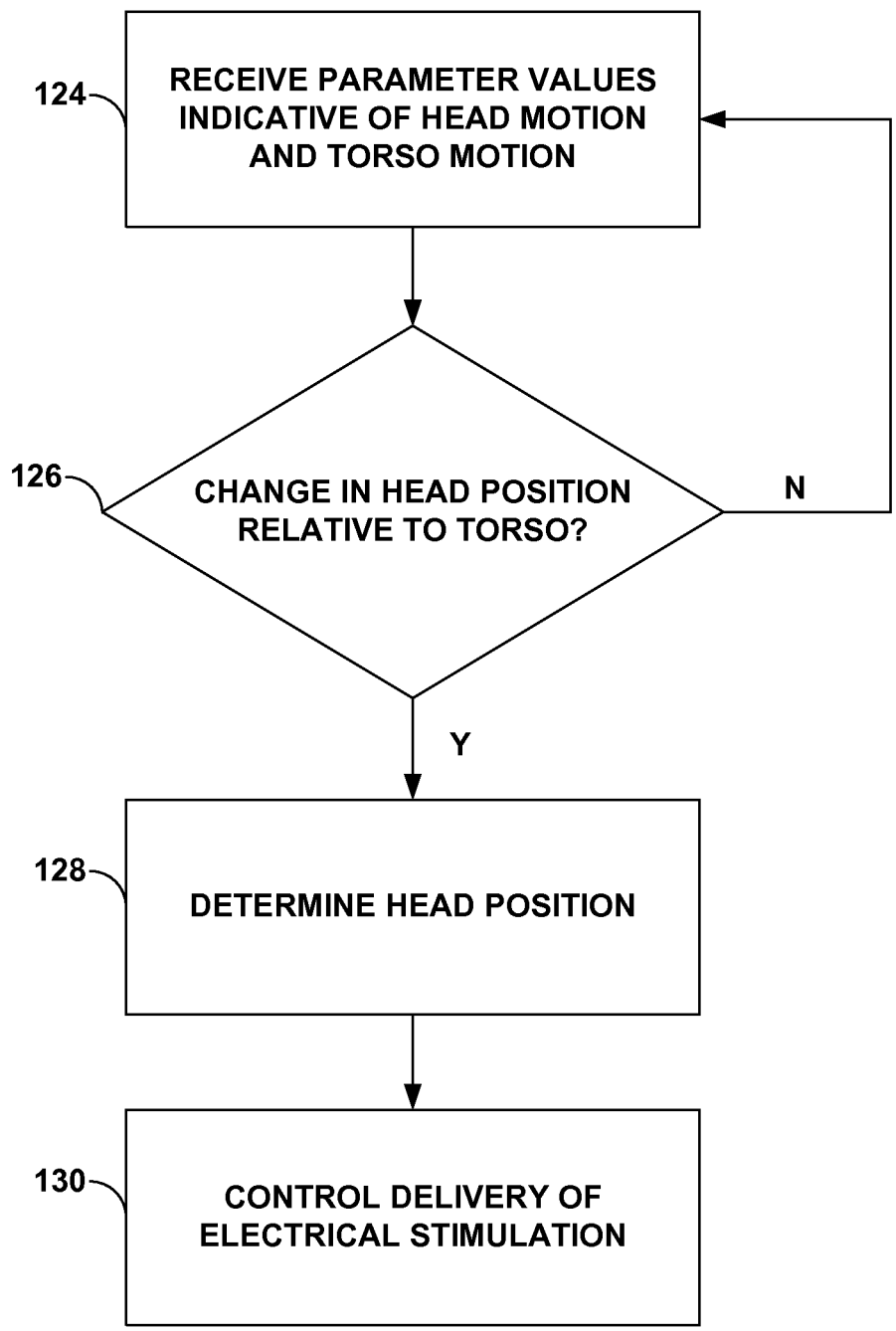
FIG. 13 is a flow diagram illustrating an example technique that includes detecting a change in head position relative to torso position of a patient prior to determining a head position of the patient and controlling delivery of electrical stimulation to the patient based on the determined head position.

FIG. 13 illustrates an example technique that may be performed by processor 44 to control delivery of electrical stimulation to patient 12 only based on detecting a change in head position relative to torso 24 of patient 12. In some examples, the probability of movement of lead 16 relative to the target tissue site is greatest when head 13 moves relative to torso 24. In other words, if both head 13 and torso 24 move together and move in similar directions, e.g., when patient 12 lies down or fully rotates the body, the probability that lead 16 may move relative to the target tissue site may be small. Thus, detecting a change in head position relative to the position of torso 24 may help to identify situations in which the probability of lead movement is greatest, and to control delivery of electrical stimulation to the target stimulation site in those situations. While FIG. 13 is described as being performed by processor 44, in other examples, a processor of another device described herein, e.g., processor 50 of programmer 22, may additionally or alternatively perform any part of the technique shown in FIG. 13 alone or with the aid of a user.

According to the technique illustrated in FIG. 13, processor 44 receives parameter values indicative of motion of head 13 and motion of torso 24 (124). For example, processor 44 may receive parameter values sensed by sensing elements 84A and 84B (FIG. 8) implanted within or positioned on head 13 and torso 24, respectively. Sensing elements 84A and 84B may, in some examples, be accelerometers that generate electrical signals indicative of the motion of head 13 and torso 24, respectively. Thus, processor 44 may, in some examples, receive one or more parameter values defining the electrical signals generated by sensing elements 84A and 84B.

Processor 44 may analyze the parameter values to determine whether patient 12 exhibits a change in position of head 13 relative to torso 24 (126). For example, in examples in which processor 44 receives parameter values indicative of motion of head 13 and torso 24, e.g., from sensing elements 84A and 84B, processor 44 may compute a difference between the parameter values indicative of motion of head 13 and the parameter values indicative of torso 24. If a significant difference exists, processor 44 may determine that head 13 has moved relative to torso 24. If, on the other hand, a significant different does not exist, processor 44 may determine head 13 has not moved relative to torso 24, e.g., that patient 12 has moved both head 13 and torso 24 together, for example, to lie down.

If processor 44 does not detect a change in head position relative to torso 24, processor 44 may continue to receive the parameter values indicative of head motion and torso motion of patient 12 (124) until processor 44 does detect a change in head position relative to torso 24. Upon detecting a change in head position relative to torso 24, processor 44 may proceed to determine the parameter indicative of head position of patient 12 (128), using any suitable technique, such as the techniques described herein. Subsequently, based on determining the parameter indicative of head position of patient 12, processor 44 may control delivery of electrical stimulation to the target stimulation site of patient 12 (130), using any suitable technique, such as the techniques described herein. For example, processor 44 may adjust one or more parameters defining a currently-selected therapy program, select a new therapy program, terminate delivery of electrical stimulation, and the like, based on determining the parameter indicative of head position.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various examples have been described. These and other examples are within the scope of the following claims.

What is claimed is:

1. A method for delivering electrical stimulation therapy to a medical patient, the method comprising:
   receiving, by one or more processors, a value for a sensed parameter indicative of head position of the patient;
   selecting, by the one or more processors, at least one therapy parameter that at least partially defines electrical stimulation and is mapped to the value for the sensed parameter, the at least one therapy parameter selected from a plurality of therapy parameters previously mapped to respective values for the sensed parameter; and
   controlling, by one or more processors, delivery of the electrical stimulation to the patient based at least partially on the selected therapy parameter.

2. The method of claim 1, wherein selecting the at least one therapy parameter comprises adjusting an intensity of the electrical stimulation based on the value for the sensed parameter indicative of head position.

3. The method of claim 1, wherein selecting the at least one therapy parameter comprises adjusting an electrode configuration that at least partially defines the electrical stimulation based on the value for the sensed parameter indicative of head position.

4. The method of claim 1, wherein receiving the value for the sensed parameter indicative of head position of the patient comprises determining the head position of the patient.

5. The method of claim 1, further comprising sensing a signal indicative of impedance of tissue of the patient between a sensing element and an electrode, wherein the method further comprises determining the value of the sensed parameter indicative of head position of the patient based on the sensed signal.

6. The method of claim 1, further comprising sensing a signal indicative of at least one parameter defining an electromagnetic field generated by an inductive coil, wherein the method further comprises determining the value of the sensed parameter indicative of head position of the patient based on the at least one parameter defining the electromagnetic field, and wherein the inductive coil is configured such that the at least one parameter defining the electromagnetic field is modulated based on a distance between a ferromagnetic sensing element and the inductive coil.

7. The method of claim 1, further comprising sensing a signal indicative of at least one of motion or position of a portion of the patient, and determining the value of the sensed parameter indicative of head position of the patient based on the sensed signal.

8. The method of claim 7, wherein sensing the signal indicative of at least one of motion or position of a portion of the patient comprises sensing a signal indicative of motion of a portion of the patient via an accelerometer.

9. The method of claim 1, further comprising detecting a change in head position of the patient, and wherein selecting the at least one therapy parameter based on the value of the sensed parameter indicative of head position of the patient comprises adjusting the at least one therapy parameter defining the electrical stimulation based on detecting the change in head position.

10. The method of claim 1, wherein selecting the at least one therapy parameter based on the value of the sensed parameter indicative of head position of the patient comprises selecting a stimulation therapy program associated with the value of the sensed parameter indicative of head position of the patient, and controlling delivery of the electrical stimulation comprises delivering electrical stimulation according to the selected therapy program to the patient.

11. The method of claim 1, further comprising, prior to receiving the value of the sensed parameter indicative of head position:
receiving data indicative of head motion of the patient;
receiving data indicative of torso motion of the patient; and
detecting a change in head position relative to torso position of the patient based on the data indicative of head motion of the patient and the data indicative of torso motion of the patient.

12. The method of claim 1, further comprising delivering the electrical stimulation to a target stimulation site, wherein the target stimulation site comprises a target stimulation site proximate to an occipital nerve of the patient.

13. An electrical stimulation system for delivering electrical stimulation therapy to a medical patient, the system comprising:
one or more processors configured to:
receive a value for a sensed parameter indicative of head position of the patient,
select at least on therapy parameter that at least partially defines electrical stimulation and is mapped to the value of the sensed parameter, the at least one therapy parameter selected from a plurality of therapy parameters previously mapped to respective values for the sensed parameter and
control delivery of the electrical stimulation to the patient based at least partially on the selected therapy parameter.

14. The system of claim 13, further comprising:
a stimulation generator configured to deliver electrical stimulation, wherein the one or more processors are configured to select the at least on therapy parameter by at least adjusting an intensity defining the electrical stimulation based on the received value of the sensed parameter indicative of head position, and to control delivery of the electrical stimulation by at least controlling the stimulation generator to deliver the electrical stimulation with the adjusted intensity.

15. The system of claim 13, further comprising:
a stimulation generator configured to deliver electrical stimulation, wherein the one or more processors are configured to select the at least on therapy parameter by at least adjusting an electrode combination of the electrical stimulation based on the received value of the sensed parameter indicative of head position, and to control delivery of the electrical stimulation by at least controlling the simulation generator to deliver the electrical stimulation according to the adjusted electrode combination.

16. The system of claim 13, wherein the one or more processors are configured to determine the value of the sensed parameter indicative of head position of the patient by at least determining the head position of the patient.

17. The system of claim 13, further comprising:
a sensing element configured to be coupled to a portion of a body of the patient;
an electrode; and
a sensing module coupled to the sensing element and the electrode,
wherein the sensing module is configured to sense a signal indicative of impedance of tissue of the patient between the sensing element and the electrode and wherein the one or more processors are configured to determine the value for the sensed parameter indicative of head position of the patient based on the signal sensed by the sensing module.

18. The system of claim 13, further comprising:
a ferromagnetic sensing element coupled to a portion of a body of the patient;
an inductive coil; and
a sensing module,
wherein the sensing module is configured to sense a signal indicative of at least one parameter defining an electromagnetic field generated by the inductive coil and wherein the one or more processors are configured to determine the value for the sensed parameter indicative of head position of the patient based on the at least one parameter defining the electromagnetic field, wherein the inductive coil is configured such that the at least one parameter defining the electromagnetic field is modulated based on a distance between the ferromagnetic sensing element and the inductive coil.

19. The system of claim 13, further comprising a sensing element configured to sense a signal indicative of at least one of motion or position of a portion of the patient, wherein the one or more processors are configured to determine the value for the sensed parameter indicative of head position of the patient based on the sensed signal.

20. The system of claim 19, wherein the sensing element comprises an accelerometer configured to sense the signal indicative of motion of a portion of the patient.

21. The system of claim 13, further comprising a stimulation generator configured to deliver electrical stimulation, wherein the one or more processors are configured to determine the value for the sensed parameter indicative of head position of the patient by at least detecting a change in head position of the patient, and wherein the one or more processors are configured to select the at least one therapy parameter based on the determined value of the sensed parameter indicative of head position of the patient by at least adjusting the at least one therapy parameter defining the electrical stimulation based on detecting the change in head position.

22. The system of claim 13, further comprising a stimulation generator configured to deliver electrical stimulation, wherein the one or more processors are configured to control delivery of the electrical stimulation by at least selecting a stimulation therapy program associated with the value of the sensed parameter indicative of the head position of the patient, and controlling the stimulation generator to deliver the electrical stimulation according to the selected stimulation therapy program to the patient.

23. The system of claim 13, wherein prior to receiving the value of the sensed parameter indicative of head position, the one or more processors are further configured to:
receive data indicative of head motion of the patient,
receive data indicative of torso motion of the patient, and
detect a change in head position relative to torso position of the patient based on the data indicative of head motion of the patient and the data indicative of torso motion of the patient.

24. An electrical stimulation system for delivering electrical stimulation therapy to a medical patient, the system comprising:

means for receiving a value for a sensed parameter indicative of head position of the patient;

means for selecting at least one therapy parameter that at least partially defines electrical stimulation and is mapped to the value of the sensed parameter, the at least one therapy parameter selected from a plurality of therapy parameters previously mapped to respective values for the sensed parameter; and means for controlling delivery of the electrical stimulation to the patient based at least partially on the selected therapy parameter.

25. The system of claim 24, wherein the means for selecting selects the at least one therapy parameter by at least adjusting an electrode configuration that at least partially defines the electronic stimulation based on the determined value of the sensed parameter indicative of head position, and the means for controlling controls delivery of the electrical stimulation by at least delivering the electrical stimulation according to the adjusted electrode configuration.

26. A non-transitory computer-readable medium comprising instructions that cause one or more processors to:

receiving, by one or more processors, a value for a sensed parameter indicative of head position of the patient;

selecting, by the one or more processors, at least one therapy parameter that at least partially defines electrical stimulation and is mapped to the value for the sensed parameter, the at least one therapy parameter selected from a plurality of therapy parameters previously mapped to respective values for the sensed parameter; and controlling, by the one or more processors, delivery of the electrical stimulation to the patient based at least partially on the selected therapy parameter.

27. The non-transitory computer-readable medium of claim 26, wherein the instructions cause the one or more processors to select the the at least one therapy parameter by at least adjusting an electrode configuration that at least partially defines electrical stimulation based on the determined value for the parameter indicative of head position.

28. The method of claim 1, wherein selecting the at least one therapy parameter comprises adjusting an intensity of one or more therapy parameters of the electrical stimulation delivered to the patient based at least partially on the adjusted one or more therapy parameters.

29. The method of claim 1, wherein selecting the at least one therapy parameter comprises selecting one of a plurality of different therapy stimulation programs for the electrical stimulation based at least partially on the selected therapy parameter.

30. The method of claim 1, further comprising:

prior to receiving the value of the sensed parameter indicative of head position, mapping a plurality of different head positions indicated by different ranges of values of the sensed parameter, wherein selecting the at least one therapy parameter comprises selecting different electrical stimulation for at least some of the different head positions indicated by the different values of the sensed parameter, and wherein controlling delivery of the electrical stimulation comprises controlling delivery of the different electrical stimulation for the different head positions based on the different values of the sensed parameter.

31. The method of claim 1, wherein the value of the sensed parameter is based at least in part on a detected movement in the head position of the patient, wherein the detected movement of the head position correlates to movement of one or more leads relative to a target stimulation site.

32. The system of claim 13, wherein to select the at least one therapy parameter, the one or more processors are configured to adjust one or more stimulation parameters of the electrical stimulation delivered to the patient based at least partially on the selected at least one therapy parameter.

33. The system of claim 13, wherein to select the at least one therapy stimulation parameter, the one or more processors are configured to select one of a plurality of different therapy stimulation programs for the electrical stimulation delivered to the patient.

34. The system of 13, wherein the one or more processors are further configured to map a plurality of different head positions indicated by different ranges of values of the sensed parameter, select the at least one therapy parameter comprising selecting different therapy parameters for at least some of the different head positions indicated by the different values of the parameter, and to control delivery of the electrical stimulation comprising the one or more processors controlling a stimulation generator, the delivery of the different electrical stimulation for the different head positions based on the different values of the parameter.

35. The method of claim 1, further comprising:

storing, in a memory, the mapping of the respective values for the sensed parameter to the plurality of therapy values, wherein selecting the at least one therapy parameter includes selecting the at least one therapy parameter from the plurality of therapy values based on the mapping stored in the memory.

36. The method of claim 1, wherein the value for the sensed parameter indicative of the head position of the patient comprises a measurement indicative of the head position of the patient relative to another portion of a body of the patient.

37. The system of claim 13, further comprising:

a memory accessible by at least one of the one or more processors, the memory configured to store the mapping of the respective values for the sensed parameter indicative of the head position of the patent to the plurality of therapy values, wherein the one or more processors are configured to select the at least one therapy parameter from the plurality of therapy values based on the mapping stored in the memory.

38. The system of claim 13, wherein the value for the sensed parameter indicative of the head position of the patient comprises a measurement indicative of the head position of the patient relative to another portion of a body of the patient.

* * * * *